United States Patent
Lampotang et al.

(10) Patent No.: US 6,597,939 B1
(45) Date of Patent: *Jul. 22, 2003

(54) METHOD AND APPARATUS FOR COORDINATING AN EVENT TO DESIRED POINTS IN ONE OR MORE PHYSIOLOGICAL CYCLES

(75) Inventors: Samsun Lampotang, Gainesville, FL (US); Paul B. Langevin, Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/081,725

(22) Filed: May 20, 1998

Related U.S. Application Data

(63) Continuation-in-part of application No. 09/026,908, filed on Feb. 20, 1998, now Pat. No. 6,370,419.

(51) Int. Cl.[7] ............................................. A61B 5/00
(52) U.S. Cl. ..................... 600/427; 600/428; 600/538; 600/539; 128/202.13; 128/202.16; 378/95
(58) Field of Search ................................. 600/411, 413, 600/427, 428, 529, 534, 538, 539; 128/200.24, 202.13, 202.16; 378/95, 98, 117, 147; 601/2–6

(56) References Cited

U.S. PATENT DOCUMENTS

| | | | |
|---|---|---|---|
| 3,871,360 A | | 3/1975 | Van Horn et al. |
| 4,123,654 A | | 10/1978 | Reiss et al. |
| 4,745,920 A | * | 5/1988 | Forssmann et al. ............ 601/4 |
| 4,991,587 A | * | 2/1991 | Blakeley et al. ............ 600/413 |
| 4,994,744 A | | 2/1991 | Glover et al. |
| 5,259,368 A | * | 11/1993 | Wiksell ............ 601/4 |
| 5,485,833 A | | 1/1996 | Dietz |
| 5,485,835 A | | 1/1996 | Vande Streek et al. |
| 6,076,005 A | * | 6/2000 | Sontag et al. ............ 600/413 |
| 6,205,200 B1 | * | 3/2001 | Boyer et al. ............ 378/101 |

FOREIGN PATENT DOCUMENTS

| | | |
|---|---|---|
| DE | 0377764 | 12/1989 |
| FR | 2604890 | 10/1986 |
| JP | 07210247 | 2/1995 |

OTHER PUBLICATIONS

Ehman et al. (1994) "Magnetic Resonance Imaging With Respiratory Gating: Techniques and Advantages" AJR:143.

* cited by examiner

Primary Examiner—Ruth S. Smith
(74) Attorney, Agent, or Firm—Saliwanchik, Lloyd & Saliwanchik

(57) ABSTRACT

The subject invention pertains to a novel method and apparatus for improving the efficacy of a medical treatment or diagnostic procedure by coordinating such treatment or procedure with at least one physiological cycle of a patient. In a specific embodiment, the subject invention pertains to a novel method of coordinating a chest x-ray with a patient's ventilatory cycle. In a specific example, this invention concerns a novel device for interfacing a ventilator and an x-ray machine to ensure that an x-ray chest image can be taken at peak insufflation of the patient. The subject invention also relates to other medical procedures including, but not limited to, cardiac output measurement, chest imaging, inhalation therapy, oxygen delivery, blood pressure measurement, extracorporel shock wave lithotripsy, and pulse oximeter optoplethysmograms. By coordinating certain medical treatments and diagnostic procedures with a patient's physiological cycle(s), the subject invention improves the quality of medical care received by the patient.

37 Claims, 16 Drawing Sheets

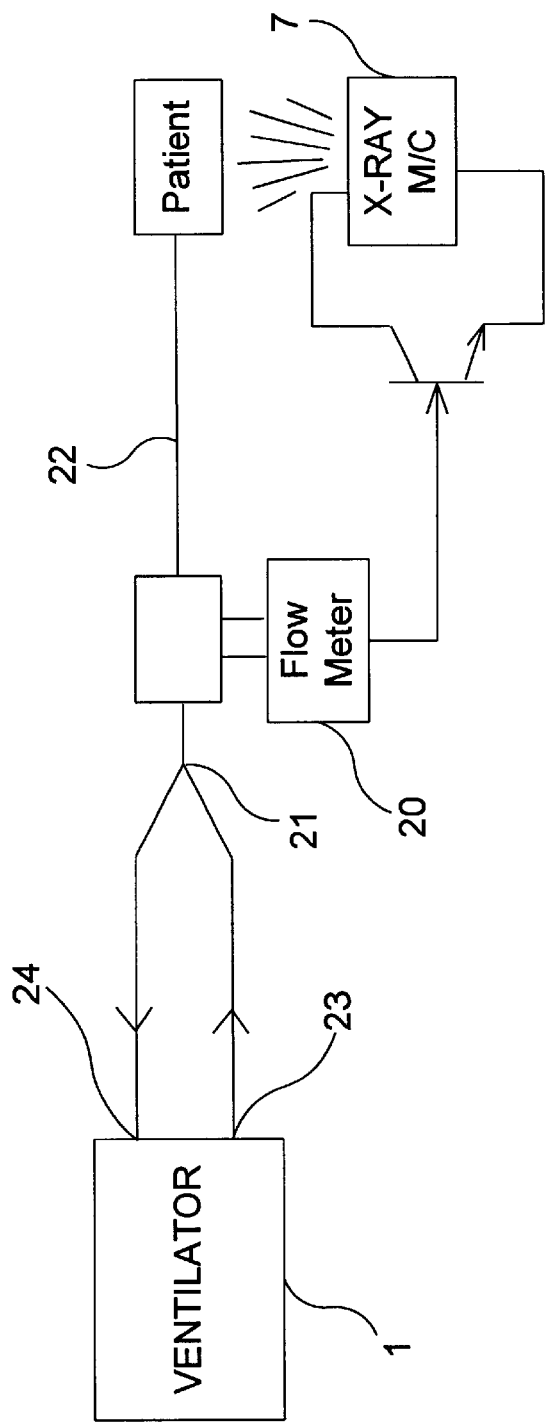
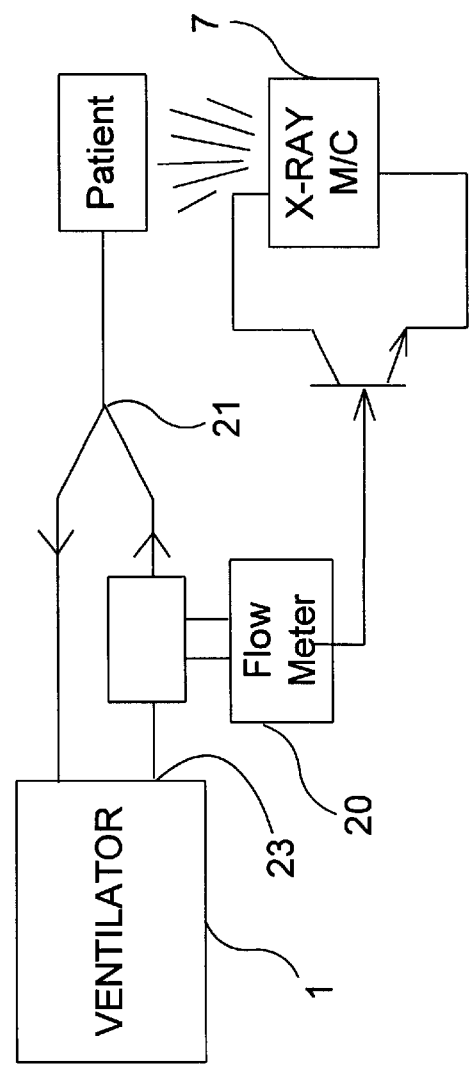
FIG. 2A
FIG. 2B

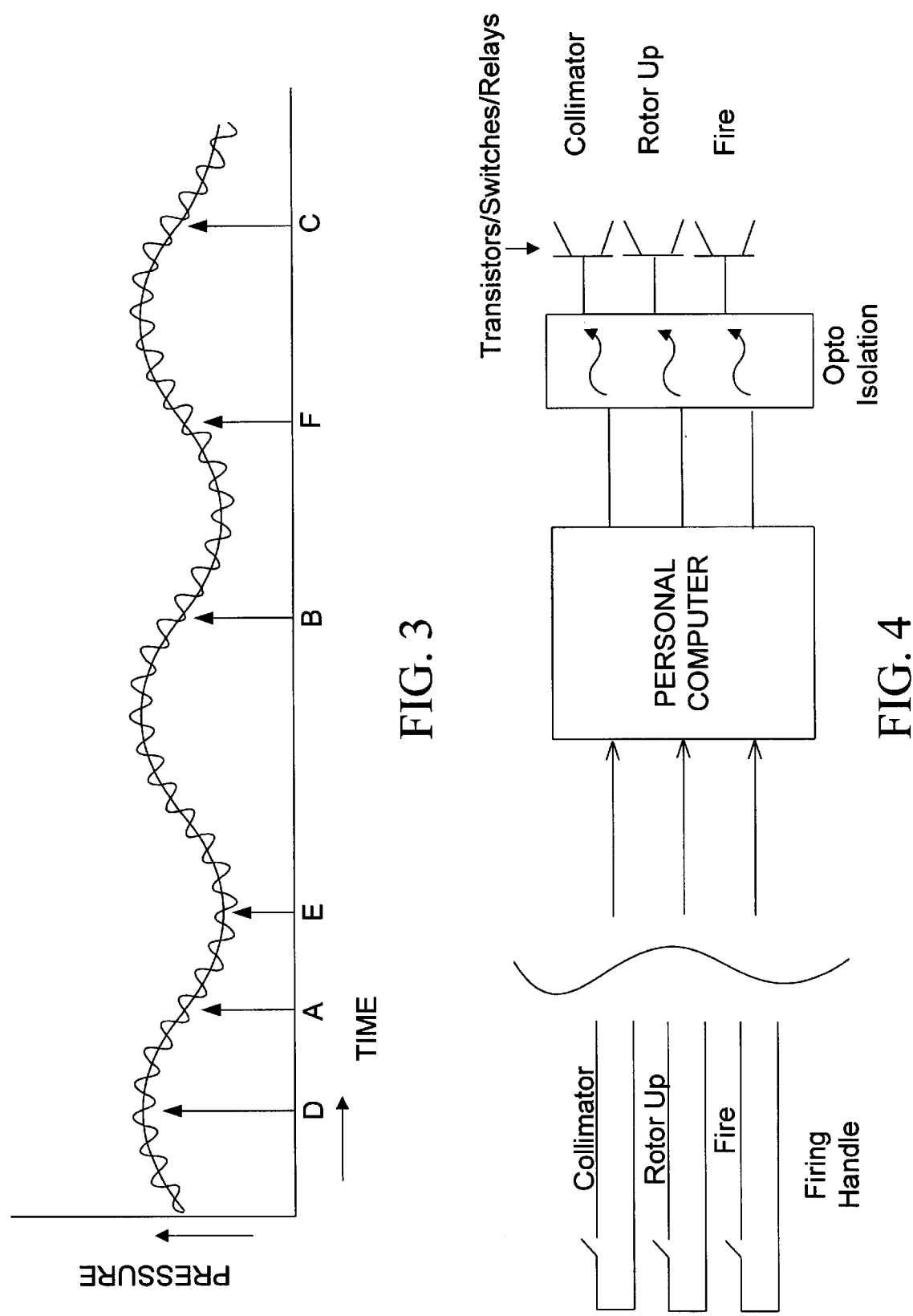

METHOD AND APPARATUS FOR COORDINATING AN EVENT TO DESIRED POINTS IN ONE OR MORE PHYSIOLOGICAL CYCLES

CROSS-REFERENCE TO A RELATED APPLICATION

This application is a continuation-in-part of U.S. application Ser. No. 09/026,908, filed Feb. 20, 1998, now U.S. Pat. No. 6,370,419 issued on Apr. 9, 2002.

BACKGROUND OF THE INVENTION

There are many medical treatments and diagnostic procedures the efficacy of which can be improved by coordinating such treatment or procedure with a patient's physiological cycles, for example a patient's breathing cycle. In many instances patients can control their breathing to assist the medical provider. However, some patients are not able to control their breathing, for example patients on ventilators. Other physiological cycles, for example the beating of a patient's heart, are typically out of the patient's control entirely. Accordingly, an apparatus which could facilitate the timing of such a medical treatment or a diagnostic procedure with respect to one or more physiological cycles of a patient would be beneficial to the patient.

As an example, chest radiographs are often taken in the intensive care unit using portable x-ray machines. These x-ray images provide important information to the clinician and, therefore, the quality of the images is important. Factors which can affect the quality of chest radiographs include: patient position and movement; ability of patient to receive and respond to instruction; penetration of the x-ray beam; and, perhaps most important, timing of the x-ray beam exposure with patient insufflation.

Typically, the highest quality chest images are attained when the image is taken at peak insufflation because there is less tissue mass per unit area, and penetration is uniform. Accordingly, patients who are able to receive and respond to instruction can be instructed to take and hold a deep breath long enough to take the required images, for example radiographs. However, for patients on a ventilator, in order to take the radiograph at peak insufflation, the person taking the radiograph must attempt to accurately time the x-ray beam exposure with the cycle of the ventilator. When the radiograph is not timed correctly, it may be less than optimal and additional costs are incurred if it is necessary to retake the radiograph. Furthermore if time is critical, the caregiver may be forced to provide care with inadequate information.

Current techniques for synchronizing the x-ray beam exposure with peak lung inflation (PLI) include placing a paper cup on the chest of a supine patient and visually anticipating PLI. This results in variable radiograph quality and the frequent need for repeat radiographs, which increases radiation exposure to the patient, personnel and material costs, delays in initiating treatment, and reduced confidence in the diagnostic information contained in the radiograph.

With respect to magnetic resonance imaging (MRI) images, a plurality of images often need to be taken of adjacent slices of the patient. When imaging parts of the body where the motion of the patient, for example due to the patient's breathing, can affect the quality of the images, care needs to be taken such that images of adjacent slices are taken with as little motion of the body between images as possible. Prior techniques for effecting MRI images of a patient's thorax and upper abdomen region have included respiratory gating (Ehman et al (December 1994) "Magnetic Resonance Imaging with Respiratory Gating: Techniques and Advantages" AJR: 143).

Accordingly, there exists a need in the art for a method and device which can ensure that chest images of patients on ventilators are taken at a desired degree of insufflation to enhance the quality of such chest images. These images can be effected by a variety of apparatus, including but not limited to, MRI machines, CAT scan machines, and PET scan machines. In particular, a device which could interface a ventilator with an x-ray machine to ensure chest radiographs are taken at peak ventilation would improve the quality of such chest radiographs and, therefore, improve the quality of care for ventilated patients.

Additional situations where the efficacy of the medical treatment or procedure can be affected by timing the treatment or procedure with respect to a desired point in the breathing cycle include, but are not limited to, inhalation therapy, oxygen ($O_2$) delivery, cardiac output (CO) measurements, blood pressure measurements, and pulse oximeter optoplethysmograms. With inhalation therapy and $O_2$ delivery, timing the delivery of the appropriate substances with respect to the breathing cycle can affect the dose administered, the amount of waste, pollution, and costs. With blood pressure measurements, CO measurements, and pulse oximeter optoplethysmograms, the timing of the measurements with respect to the breathing cycle can affect, for example, the precision of the readings.

Accordingly, there exists a need in the art for a method and device which can coordinate a medical treatment or diagnostic procedure with respect to one or more physiological cycles of a patient in order to enhance the efficacy of the medical treatment or diagnostic procedure.

BRIEF SUMMARY OF THE INVENTION

The subject invention pertains to a method and apparatus for coordinating a medical treatment or diagnostic breath procedure with respect to one or more physiological cycles of a patient. The subject invention is applicable to human or animal patients. In a specific embodiment, the subject invention pertains to a novel method of coordinating a chest radiograph with the ventilatory cycle. In another specific embodiment, the subject invention relates to a novel method of coordinating a medical treatment or diagnostic procedure with the pumping of the patient's heart, for example in order to remove artifacts produced by the pumping of the heart.

The methods and apparatus of the subject invention are particularly advantageous for use in chest radiography. In a specific example, the subject invention concerns a novel device for interfacing a ventilator and an x-ray machine to ensure that an x-ray chest image can be taken at a desired degree of ventilation of the patient, for example, peak lung inflation. The interfacing of a ventilator and an x-ray machine, according to the subject invention, improves the chest image quality and, therefore, improves the quality of medical care received by the patient. In a specific embodiment, the taking of a radiograph can be accomplished by emulating an x-ray machine firing handle with software, for example, on a notebook personal computer. In a preferred embodiment, the subject invention utilizes a standard firing handle currently used with x-ray machines, in order to minimize the retraining required by operators. The use of the standard firing handle in accordance with the subject invention can be made to mimic its current use with the exception that instead of the operator attempting to time an event with the ventilatory cycle, software controls the timing of such event.

Further embodiments of the subject invention pertain to, for example, the delivery of inhalants, delivery of oxygen ($O_2$), blood pressure measurements, cardiac output (CO) measurements, pulse oximeter optoplethysgrams, and further imaging techniques. With respect to the delivery of inhalants and the delivery of $O_2$, the method and apparatus of the subject invention can improve the efficiency of the delivery of the appropriate substance, improve the accuracy of administering the correct dose, and reduce waste and costs. With respect to blood pressure measurements, CO measurements and pulse oximeter optoplethysgrams, the method and apparatus of the subject invention can improve the precision and consistency of the measurements by timing the measurements with respect to the breathing cycle of a patient.

BRIEF DESCRIPTION OF THE DRAWINGS

FIG. 2A shows a block diagram of an embodiment of an apparatus to interface a ventilator and an x-ray machine wherein a flowmeter positioned at the Y-piece is utilized, in accordance with the subject invention.

FIG. 2B shows a block diagram of an embodiment of an apparatus to interface a ventilator and an x-ray machine wherein a flowmeter positioned at the ventilator-inspiratory hose connection is utilized, in accordance with the subject invention.

FIG. 3 illustrates an idealized, not to scale, schematic of the variation of the central venous pressure as a function of time due to the effect of respiration.

FIG. 4 shows schematically an embodiment of a computer/x-ray machine interface in accordance with the subject invention.

DETAILED DISCLOSURE OF THE INVENTION

The subject invention pertains to a method and apparatus for coordinating a medical treatment or a diagnostic procedure, with respect to one or more physiological cycles of a patient. The subject invention is applicable to human or animal patients. In particular, patients on a ventilator can benefit from the subject invention.

In a specific embodiment, the subject invention pertains to a novel method for timing a chest image with the ventilatory cycle. The subject method and apparatus can ensure images of the chest are taken at a desired degree of insufflation of the patient and, therefore, improve the quality of such chest images. Furthermore, the subject invention can enable chest images to be taken when the lungs are essentially motionless, for example at a zero-flow crossing, resulting in higher quality images. In a specific embodiment, this invention concerns a novel device for interfacing a ventilator and an x-ray machine, to ensure that an x-ray chest image can be taken at peak lung inflation of a patient and thereby enhance the quality of such an x-ray chest image.

The subject invention also pertains to interacting with other imaging apparatus such as PET scan machines, CAT scan machines, and MRI machines. Each of these apparatus have unique attributes and, accordingly, the subject invention can be adapted to interface with each one. For example, MRI machines typically take a plurality of images over a long period of time, wherein a multitude of thin "slices" of the patient are imaged over this period of time. Each "slice" is imaged during a fraction of the breathing cycle, such that the subject device can be utilized to image each consecutive "slice" at the same point in the cycle, or during the same part of the cycle, in consecutive cycles of the patient's breathing. This can result in higher quality images because the body will be in nearly the same position for each image, as opposed to images taken at all different points in the breathing cycle.

Figure 1:
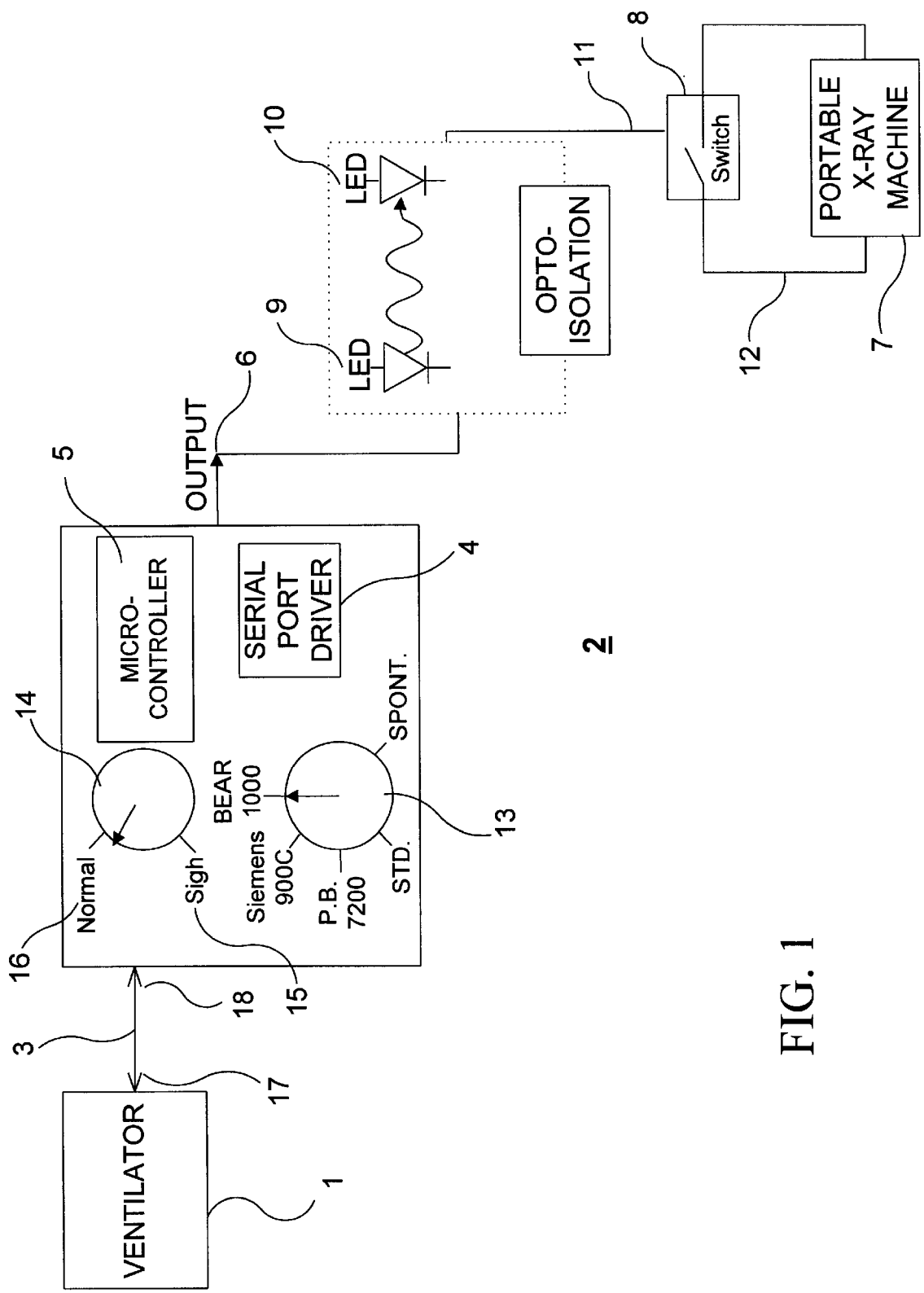
FIG. 1 shows a block diagram of an embodiment of an apparatus to interface a ventilator and an x-ray machine wherein a signal from the ventilator is utilized, in accordance with the subject invention.
Figure 5:
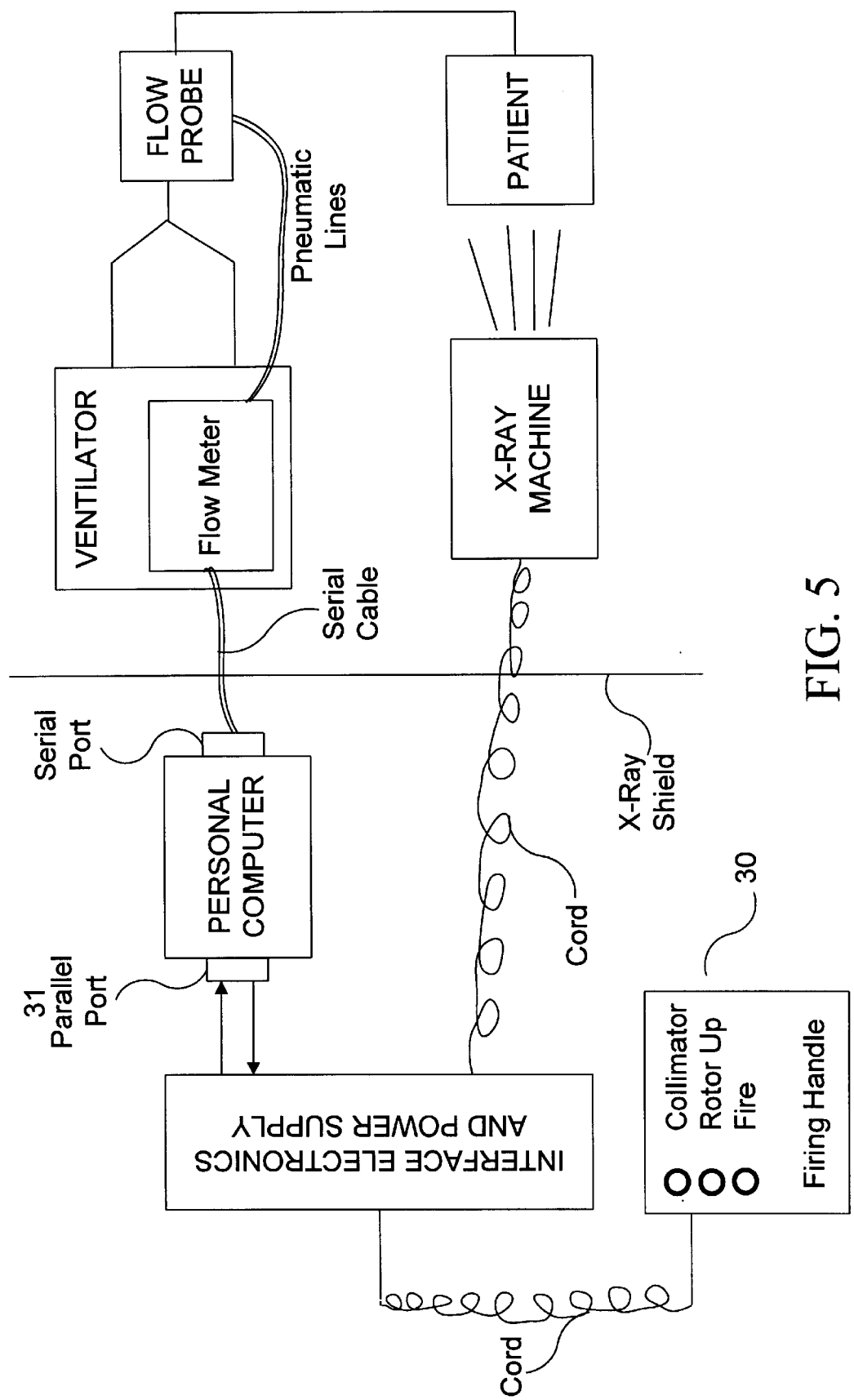
FIG. 5 shows a block diagram of an embodiment of a system which synchronizes x-ray beam exposure with peak lung inflation, in accordance with the subject invention.

Referring to FIG. 1, a block diagram of an apparatus for interfacing a ventilator and an x-ray machine is shown in accordance with the subject invention. Ventilator 1 can retrieve and send data to interface 2 on, for example, a serial communication link 3. A first end 17 of serial communication link 3 can connect to the ventilator, for example to the serial port (RS-232) of the ventilator, and a second end 18 of serial communication link 3 can connect to the interface 2, for example to a serial port driver 4. Serial port driver 4 can be linked to microcontroller 5. Microcontroller 5 can have an output 6 to, for example, an x-ray machine 7. In a specific embodiment, output 6 can be connected to a switch 8, where upon receiving an appropriate signal switch 8 closes, effecting the taking of a radiograph.

In order to minimize the risk of injury to the patient, the subject invention can provide a means for isolating ventilator 1 and interface 2 from the electrical circuitry of x-ray machine 7. This isolation means can include, for example, RF circuitry, IR detectors, LED's, lasers, photodetectors, or other appropriate devices which can send and receive a signal without a direct wire connection. In a preferred embodiment, output 6 can be connected to first LED 9, where upon first LED 9 receiving an appropriate signal from interface 2, first LED 9 can send a light signal to second LED 10 which can then send an appropriate signal 11 to, for example, portable x-ray machine 7. First LED 9 and second LED 10 used in this way act to isolate ventilator 1 and interface 2 from the electrical circuitry of x-ray machine 7. This isolation, referred to as opto-isolation, isolates the patient from the electrical circuitry of x-ray machine 7 and, therefore, improves patient safety. In a specific embodiment, the output signal 11 from second LED 10 can be sent to switch 8 which then switches x-ray machine 7 on and off, for example via cable 12. In addition, cable 12 can, for example, be connected to a toggle switch on an x-ray machine which can be operated by the x-ray technician.

The subject invention allows microcontroller 5, having access to the status of ventilator 1, to effect the taking of a chest image by sending an appropriate output signal 6 to, for example, an x-ray machine. In a preferred embodiment, microcontroller 5 can be connected to a ventilator model selector switch 13, for example a manual switch on the interface, which can have settings corresponding to existing ventilator models. These ventilator models can include, for example, Siemens 900C, P.B. 7200, BEAR 1000, and STD. By setting switch 13 to a particular model, the correct serial communication protocol can be utilized by microcontroller 5 to monitor signals from ventilator 1 corresponding to the status of ventilator 1 such that microcontroller 5 can effect the taking of a radiograph at a desired degree of ventilation of the patient, for example at peak lung inflation.

For patients who are able to receive a sigh breath, in order to realize peak lung inflation, it is preferred to take a chest radiograph during a sigh breath. A sigh breath has approximately three times the tidal volume as a normal breath and, therefore, taking a chest radiograph during a sigh breath improves the quality of the resulting chest radiograph. However, some patients are unable to receive a sigh breath because of medical reasons. In a preferred embodiment, interface 2 can have a sigh switch 14 which, when set to sigh 15, enables microcontrollers 5 to signal ventilator 1 to administer to the patient a sigh breath and, subsequently, effect the taking of a radiograph during the sigh breath. When sigh switch 14 is set to normal 16, the patient is not given a sigh breath and an a radiograph can be taken at a desired degree of ventilation, for example at peak lung inflation for a regular tidal volume breath.

In an additional embodiment, interface 2 can have a switch which indicates the degree of insufflation of the patient at which a chest image is to be taken. This switch can allow a chest image to be taken at, for example, minimum insufflation of the patient. Accordingly, the subject invention can enable a comparison of a chest image at minimal insufflation and a chest image at maximum insufflation. This switch can have settings of, for example, minimum, 25% maximum, 50% maximum, and maximum insufflation. To coordinate with sigh switch 14, the switch which indicates the degree of insufflation can also have a sigh setting for use when a sigh breath is desired.

Figure 9A:
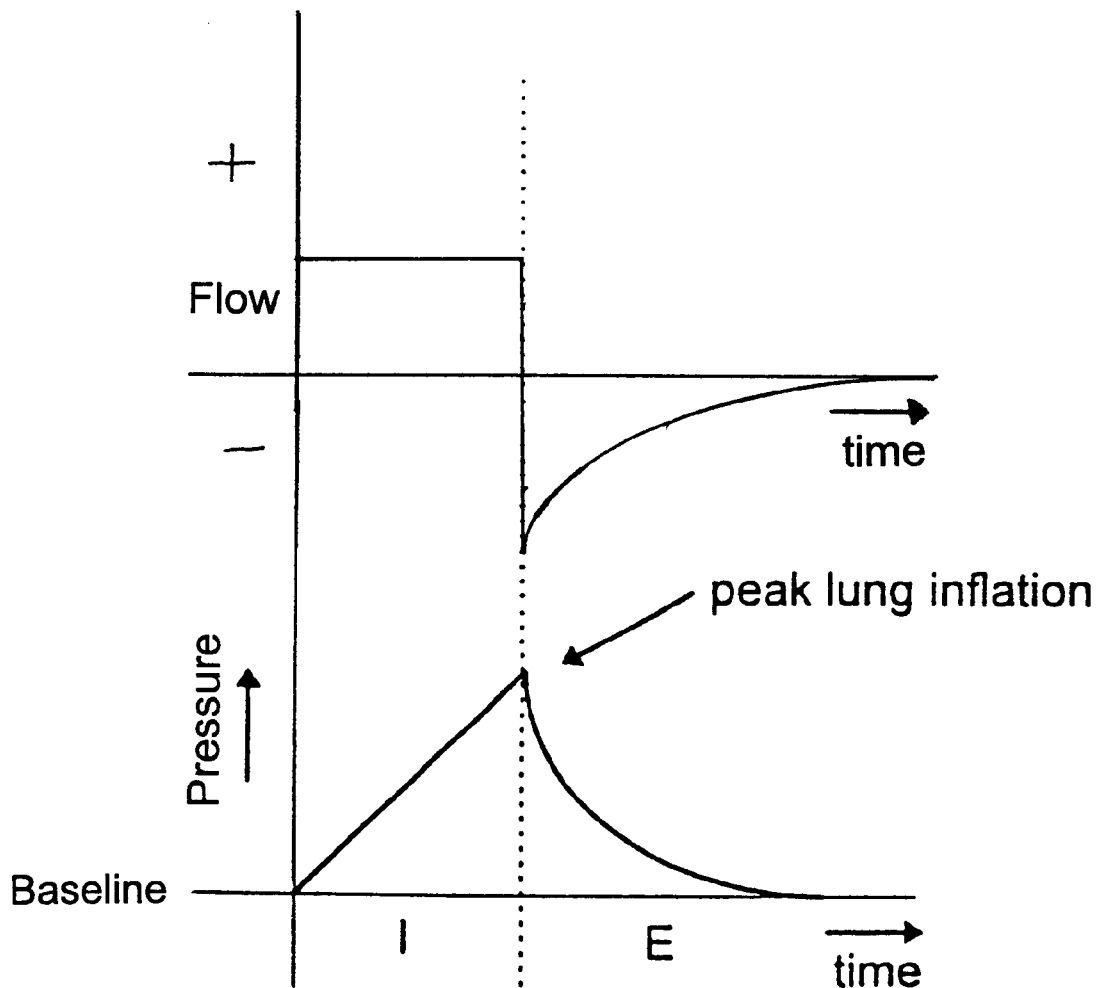
FIG. 9A illustrates a patient's airway pressure versus time during inspiration (I) and expiration (E), during positive pressure ventilation.
Figure 9B:
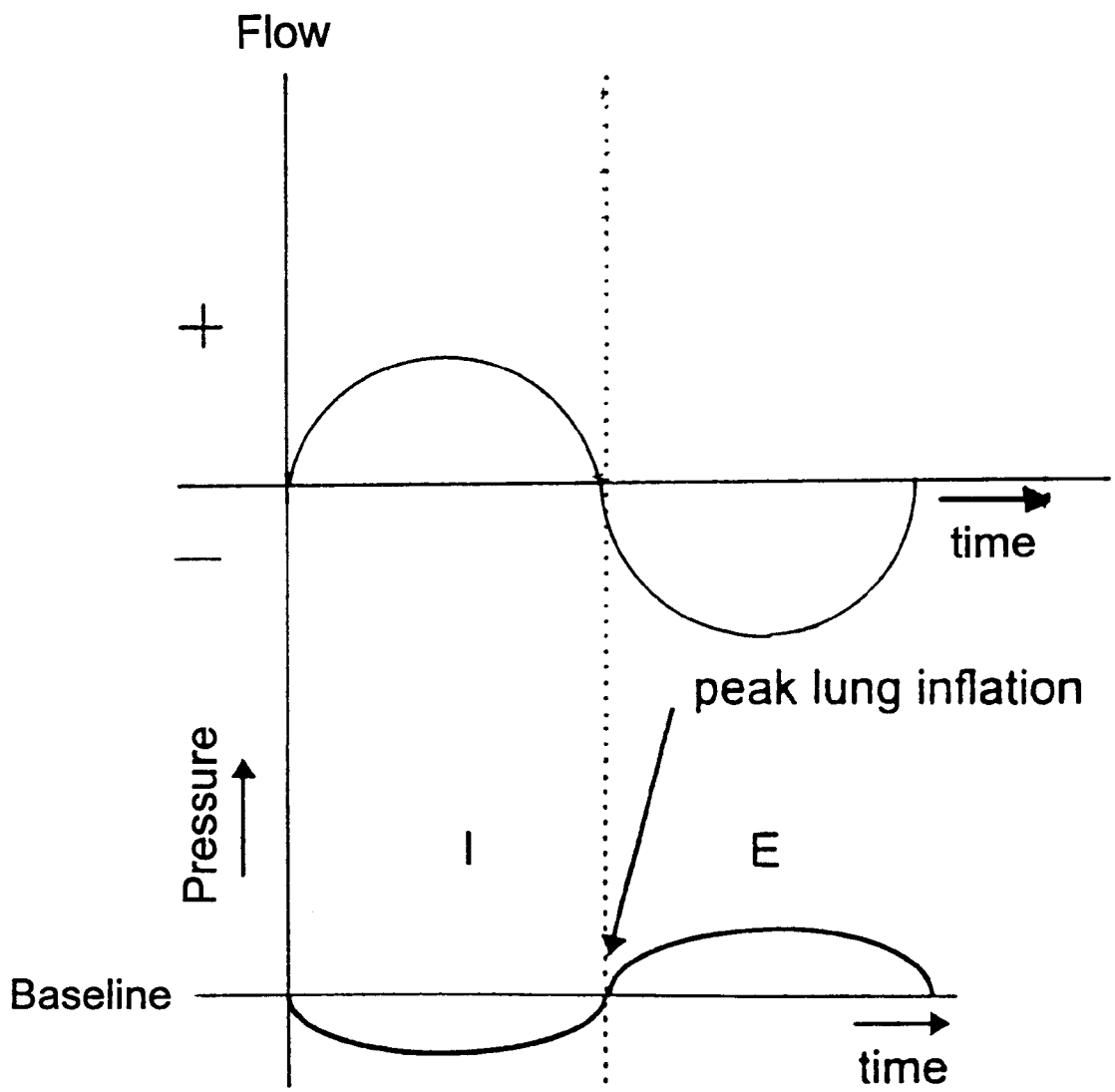
FIG. 9B illustrates a patient's airway pressure versus time during inspiration (I) and expiration (E), during spontaneous ventilation.

In a further embodiment, interface 2 can have a setting, for example on the ventilator model selector switch 13, for patients who are spontaneously breathing and, therefore, are not on a ventilator. Alternatively, interface 2 can have an override switch for patients who are not on a ventilator. For a patient who is spontaneously breathing, interface 2 can receive a signal from a means for determining the degree of insufflation of a patient. Thereby, interface 2 can effect the taking of a chest image at peak insufflation, even for a patient who is spontaneously breathing and, therefore, not on a ventilator. In a specific embodiment, particularly useful in situations where a patient is unconscious and spontaneously breathing, an algorithm is utilized which automatically distinguishes between patients who are spontaneously breathing and patients who are breathing under positive pressure. The algorithm can, for example, monitor pressure in the airway. Referring to FIGS. 9A and 9B, the airway pressure profiles are different for positive pressure breathing (FIG. 9A) and spontaneous breathing (FIG. 9B). For example, a spontaneously breathing patient (FIG. 9B) can have a positive flow of air when the airway pressure is below the patient's baseline pressure, while a positive pressure ventilated patient (FIG. 9A) can have a positive flow when the patient's airway pressure is above the patient's baseline pressure. The peak lung inflation detection algorithm can be different for positive pressure ventilation and spontaneous ventilation. Accordingly, being able to automatically determine whether a patient is under positive pressure ventilation or is spontaneously breathing allows automatic selection of the appropriate algorithm for detecting peak lung inflation.

There are multiple techniques the subject device can utilize to determine a particular point in the breathing cycle of a patient, for example peak lung inflation. If, for example, an electronic ventilator is able to generate an electrical signal each time a ventilated breath has been administered, then peak lung inflation can be ascertained by monitoring this electrical signal via, for example, a communications port. This technique requires a signal from a ventilator where the communications protocol is known to the subject device. Without a standardized communication protocol for ventilators, the make, model and version of the ventilator needs to be known to assure proper communication since the serial communication protocol can be different for each ventilator. Accordingly, a technique which is compatible with all types of ventilators, electronic or pneumatic, would be preferred and more readily accepted by clinicians.

Many ventilators currently in use are pneumatic and do not have microprocessor or electrical power supplies to enable the generation of an electrical signal corresponding to the point in a patient's ventilatory cycle. In a preferred embodiment, the x-ray machine synchronization device utilizes a flow/pressure sensor probe (FloTrak, Novametrix) positioned between the breathing circuit and the airway device to infer peak lung inflation. The use of a flow/pressure sensor probe allows the subject device to function with essentially any ventilator, for example electronic or pneumatic. The device does not have to be specifically designed for the particular ventilator because the flow and pressure sensor probes are positioned at the airway and monitor the flow of gas to and from the patient as well as the airway pressure.

Further embodiments of the subject invention can enable the capture or identification of any given point in the breathing cycle, for example a desired phase of a breath, using an apparatus such as a ventilator, a flowmeter positioned either at the Y-piece, at the ventilator expiratory hose connection, or at the ventilator-inspiratory hose connection, a pressure gauge in the airway, or any monitor or instrument that allows positive identification of a point in the breathing cycle. In another embodiment, a $CO_2$ monitor can monitor the amount of $CO_2$ being exhaled by a patient, where low $CO_2$ levels are present when the patient is breathing in, higher $CO_2$ levels are present when a patient is breathing out, and a spike in $CO_2$ level can occur when the patient starts to breathe out. Further embodiments can utilize a transthoracic belt tied around a patient's chest which can act as a strain gauge reacting to the expansion of the patient's chest such as to indirectly give the volume of gases in the lungs, or a transthoracic impedance plethysmograph can monitor the electrical impedance across two electrodes placed on either side of the chest where the impedance changes with the expansion of the patient's chest such as to indirectly give the volume of gases in the lungs. Accordingly, events can be triggered to occur at any desired point in the breathing cycle. The instrument or monitor for identifying a point in the breathing cycle can be, for example, a Propaq portable monitor, a Hewlett Packard Merlin, or a Datex AS/3.

Referring to FIG. 2A, in a specific embodiment of the subject invention, instead of an electronic signal from a ventilator being utilized to detect the degree of a patient's insufflation, a flowmeter 20, for example placed at a patient's Y-piece 21, can be used to detect the degree of insufflation. In alternative embodiments, flowmeter 20 can be placed at either the inspiratory port/hose connection 23 or the expiratory port/hose connection 24. Advantageously, the use of flowmeter 20 allows the degree of insufflation to be determined even when using an entirely pneumatic ventilator. Accordingly, the use of flowmeter 20 allows an x-ray machine 7 to be triggered from any ventilator, electronic or pneumatic. A specific flowmeter which can be utilized according to the subject invention is a Novametrix FloTrak flowmeter. In a specific embodiment, the flowmeter probe can be left in the circuit, between the breathing circuit Y-piece 21 and the endotracheal tube 22, at all times, thus eliminating the necessity of inserting and removing the flowmeter each time an x-ray is taken.

In a preferred embodiment, flowmeter 20 can be placed inside ventilator 1, reducing the risk of damage or user misuse. However, referring to FIG. 2B, if flowmeter 20 is moved to either the inspiratory port/hose connection 23, the expiratory port/hose connection 24, or the inside of ventilator 1, the zero flow crossing may not be as clearly defined as when flowmeter 20 is placed at Y-piece 21 because flow can be unidirectional rather than bidirectional. In this case, the algorithm can be changed to a predictive one, where the cycle time of each breath is estimated, for example, by measuring the time between two peak inflations. Accordingly, the next peak inflation is predicted based on the cycle time. The efficacy of this method is optimum when the cycle time is regular, which is often the case for mechanical ventilation.

In a specific embodiment of the subject invention, in order to enhance the quality of images of a patient's thorax and upper abdominal region, for example MRI images, continuous flow apneic ventilation (CFAV) can be utilized. With CFAV, a continuous positive pressure flow of gases, for example air, is administered into a patient's airway such that a sufficient amount of air is continuously supplied to the patient. The air can be administered through a tube such that once the air enters the lungs, it is pushed out of the airway by the new air entering the airway. Advantageously, the lungs do not need to move with CFAV such that a patient's lungs and, therefore, thorax do not move appreciably. Accordingly, images, for example MRI images, can be effected while the thorax region is essentially motionless, resulting in high quality images in a significantly shortened time.

In another specific embodiment of the subject invention, CFAV can be utilized in conjunction with extracorporel shock wave lithotripsy (ESWL), where ESWL pertains to the pulverizing of kidney stones with shock waves without surgical incision. Currently, the patient is moved until the kidney stone is at the focus of the shock waves, referred to as targeting, and then the shock waves are administered. During ESWL, movement of the kidney stones due to the patients breathing can make targeting the shock waves more difficult. In particular, when the patient's lungs expand and contract the kidney stone can often move up and down, creating a moving target. Accordingly, by utilizing CFAV during ESWL the patient's lung are essentially motionless and, therefore, the kidney stone is more stationary and easier to target. The use of CFAV can significantly reduce the time required to perform ESWL and also minimize collateral damage to healthy surrounding tissue.

In an additional embodiment of the subject invention, high frequency ventilation can be utilized in conjunction with ESWL. High frequency ventilation can provide the patient with sufficient oxygen while minimizing the motion of the patient's thorax region because the range of motion of the lungs during ventilation is reduced.

In an additional embodiment of the subject invention, a cardiac output curve can be shot off a precise trigger from a ventilator breath. A cardiac output curve indicates the amount of blood the heart is pumping per minute. One method for producing a cardiac output curve is by cardiac thermo-dilution wherein one injects a cold fluid into an artery, for example at point A, near the output of the heart and then monitors the temperature of the fluid passing through the arterial system, for example at point B, further away from the heart than point A where the cold fluid was injected. A temperature versus time curve taken at point B can provide information which can indicate the cardiac output of the patient. By triggering the cardiac output curve with the breathing cycle of the patient, the precision of the cardiac output measurement can be enhanced. The subject invention can be utilized to perform cardiac output curves for patients on a ventilator and for patients not on a ventilator.

The subject invention also relates to the removal of artifacts produced by the pumping of the heart. For example, a device in accordance with the subject invention can monitor a patient's EKG and take a measurement at the same point in the heart's pumping cycle such as to minimize any artifact from the beating of the heart. In a preferred embodiment, the measurement can be taken at the QRS complex of the EKG each time.

Figure 6:
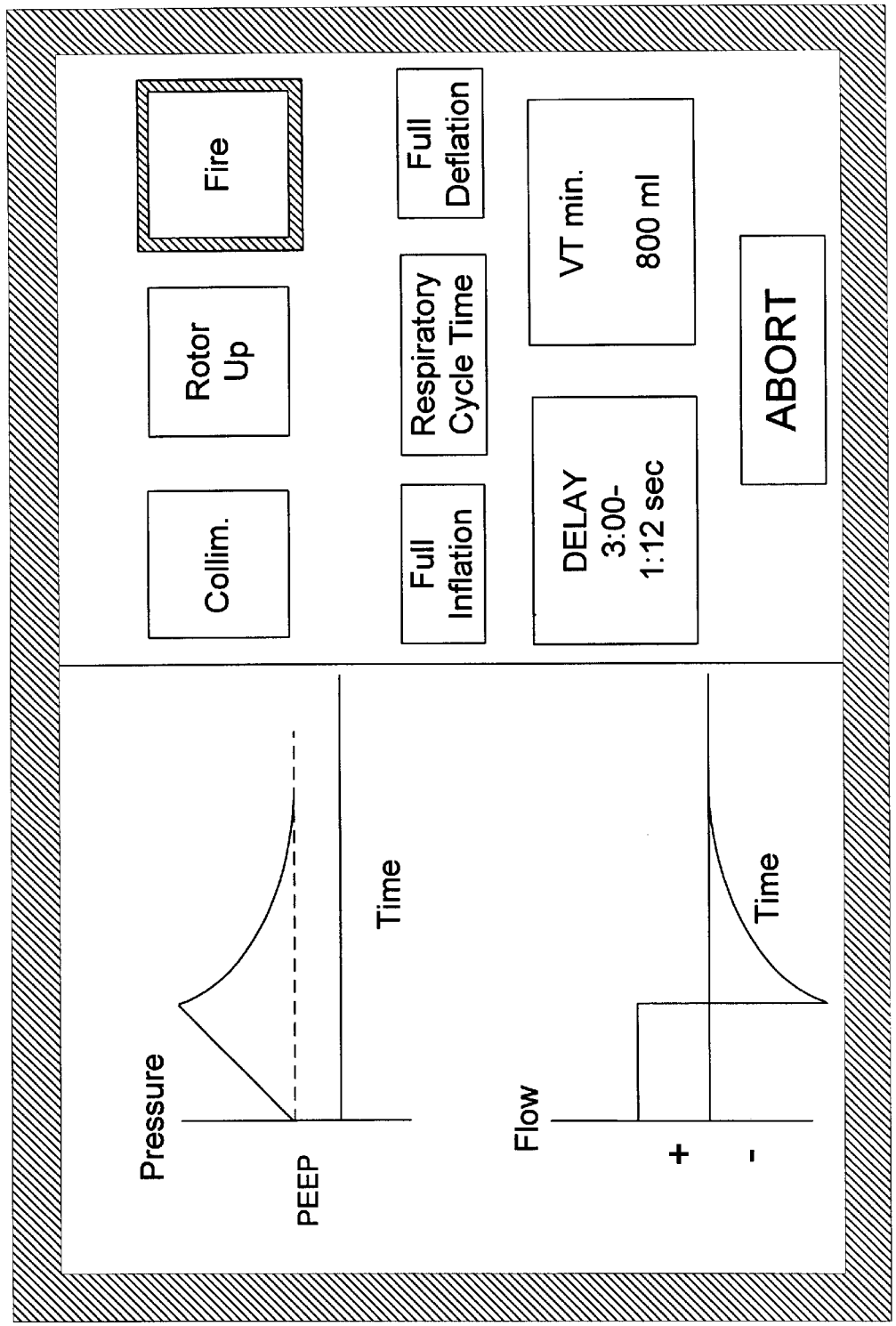
FIG. 6 illustrates an embodiment of a computer screen display in accordance with the subject invention.

Additional embodiments of the subject invention can be utilized to trigger an event, for example, inhalation therapy, at some desired point in the breathing cycle, for example, peak inflation, pause, expiration, etc. In a specific embodiment, the inhalation therapy can relate to aerosols, for example albuterol. Similarly, the system can also be used in $O_2$ conservers. For example, $O_2$ can be delivered only during inhalation which can conserve $O_2$ because $O_2$ is not delivered during exhalation. The delivery of aerosol inhalants into the pulmonary tree can be improved by timing the delivery with respect to a ventilator breath, because the flow passages are fully opened at peak inflation and the aerosol molecules can therefore reach further into the pulmonary tree. Accordingly, it might be preferred to start the aerosol delivery at the beginning of inhalation rather than the end of inhalation. Alternatively, it might be preferred to have the delivery of the aerosol occur during the entire inhalation period, i.e., the flow of gas from the ventilator acts as an additional propellant for the aerosol helping the aerosol molecules reach deeper within the lungs. It might be preferred to start the delivery of the aerosol midway or partway in the process of inhalation. Conversely, one can stop aerosol therapy, especially for expensive aerosols, during exhalation as the flow of gases away from the patient's lungs will tend to drive the aerosol molecules away from the lungs, thus preventing waste of expensive aerosol. In any of these cases, triggering the aerosol delivery to specific parts of the breathing cycle can be beneficial.

The subject invention can also be utilized to remove respiratory artifacts from signals affected by the respiratory cycle. For example, it is well known that respiration introduces artifacts in the measurement of blood pressure, for example, the central venous pressure or arterial pressure, or the pulse oximeter optoplethysmograms. FIG. 3 illustrates roughly the variation in the central venous pressure as a function of time due to the effect of respiration. The shorter time period signal represents the central venous pressure, while the longer time period signal represents the effect of respiration. Referring to FIG. 3, points A, B, and C are breath synchronized CVP measurement points which are precise and not susceptible to variation due to a respiratory effect. Points, D, E, and F are nonsynchronized, random samples, suffering from respiratory artifact.

Ventilators are often turned off during certain measurements in order to eliminate the respiratory artifact. After being turned off during the measurement, a caregiver can forget to turn the ventilator back on, sometimes with dire consequences. The subject invention can allow the measurement to be taken without turning the ventilator off, thus allowing for continuous ventilation, and improving patient safety. By timing a measurement to be taken at the same point of each breath, the respiratory artifact can be eliminated and measurements can be more consistent. For example, the effect of respiration on central venous pressure (CVP) or pulmonary artery pressure (PAP) is very pronounced. By timing the measurement to occur at any given point in the breathing cycle, for example the start of inhalation, the respiratory artifact can be reduced. Advantageously, in accordance with the subject invention, a CVP measurement can always be taken at the same point in the breath cycle. Therefore, the CVP trace or measurement is steadier.

The subject invention also pertains to the coordination of a medical treatment or diagnostic procedure with respect to a plurality of physiological cycles of a patient, for example the breathing cycle and the cardiac cycle. In a specific embodiment, a CVP or PAP measurement can be triggered on the first QRS complex of the patient's EKG following each of a plurality of peak lung inflation detections. Since the cardiac rate is usually much higher than the breathing rate and the effect of the cardiac cycle more pronounced then the effect of the breathing cycle on a CVP or PAP measurement, taking the CVP or PAP readings on the first QRS complex just after peak inflation can improve the precision of the measurement by essentially eliminating the effect of the cardiac cycle and greatly reducing the effect of the breathing cycle.

The subject x-ray machine synchronization device can be a combination of hardware and software designed to be placed between a patient and an x-ray machine. The device can work whether the patient is breathing spontaneously, under CMV (Controlled Mechanical Ventilation), or under any other mode of assisted ventilation such as CPAP (Continuous Positive Airway Pressure) and PSV (Pressure Support Ventilation). The subject device can use pressure and/or flow data from a probe, placed at the endotracheal tube, face mask, or other airway device, to determine when a patient's lungs are fully inflated and can subsequently send appropriate signals to the x-ray machine to take a radiograph of the patient. Since this entire process of synchronization and x-ray machine triggering is controlled by the device itself, the x-ray machine operator can initiate the process, for example, through an x-ray firing handle or a graphical interface implemented on a PC. Furthermore, the device can be placed in a shielded location from which an operator can safely initiate the x-ray machine synchronization process.

Current portable x-ray machines, for example the General Electric model GEAMX4, utilize a firing handle to facilitate the taking of a radiograph. On a typical firing handle, a first switch can turn on a collimator light used for aiming the x-ray machine. A second switch, for example a button referred to as "rotor-up," can "arm" the x-ray machine and charge the capacitors that power the x-ray machine. Finally, a third switch, for example a button referred to as "fire," can discharge the capacitors producing the x-ray beam. There is usually a delay, typically 2.5 seconds, between pressing the "rotor-up" button and the "fire" button because it can take some time for the capacitors to charge.

In a specific embodiment of the subject invention, the firing of an x-ray machine is accomplished with a "fire" button on a user interface, for example implemented graphically on a notebook personal computer (PC) as shown in FIG. 6. For example, when an operator clicks on the "rotor-up" button with the mouse, the "rotor-up" switch equivalent, for example a transistor, can be closed. In a specific embodiment, one or more electro-mechanical relays can be utilized as the "rotor-up," "fire," and/or "collimator" switch equivalent. There can be a fixed delay (e.g., 3 seconds) between the transistor/relay/switch representing the "rotor-up" switch closing and the "fire" switch becoming enabled such that the algorithm looking for peak lung inflation, where the x-ray machine is fired upon peak inflation, becomes active. This delay ensures that the capacitors are fully charged and able to power the x-ray source when the algorithm detects peak inflation. Without the delay, peak lung inflation might occur, for example, 1/100 of a second after "rotor-up" causing the "fire" button to close without a radiograph being taken because of insufficient charging of the capacitors. The cord linking the firing handle to the x-ray machine can be, for example, a regular phone cord used to link a phone set to a hand set. The cord should be at least 10 feet long and can be coiled like a telephone cord.

In a specific embodiment of the subject invention,the functionality of the x-ray firing handle can be emulated by software. FIG. 4 shows schematically an embodiment of a computer/x-ray machine interface in accordance with the subject invention. Referring to FIG. 4, the three switches in the firing handle, collimator, rotor up, and fire, can each be connected to, for example, a bit on a parallel port. By monitoring the status of each switch in real time, the inputs from a user can be implemented, transparent to the user. The status of each bit will change from high to low, or vice versa, depending on the logic, as each switch is opened or closed, on the firing handle. The software can also have a monitoring section on its graphical user interface to determine which buttons on the firing handle have been pressed by the user.

FIG. 5 shows a block diagram of a specific embodiment of a system to synchronize x-ray beam exposure with peak lung inflation. Referring to FIG. 5, when the user presses the collimator switch, the software can sense the action in real time and instantaneously turn on a transistor/relay/switch which turns on the collimator light. When the user presses the rotor up switch, the button on the PC display can indicate that the user has pressed the rotor up switch and the switch controlling the rotor-up function can close instantaneously to start the charging of the capacitors. A three second timer can start counting down. The actual delay will depend on how long the capacitors supplying the x-ray tube take to charge up, in this case 2.5 seconds. If a peak lung inflation occurs during the delay period and the user has pressed the "fire" button, nothing will happen until the next full lung inflation after the 3 second delay has elapsed. When the collimator switch is pressed by the user, the button on the PC display representing the collimator switch, can reverse sides or change color to indicate that the collimator switch has been triggered. A window on the PC display, as shown in FIG. 6, that shows the elapsed time in the time delay may also be useful as it would enable the user to know that the delay has not fully elapsed and therefore the system will not fire.

When the user presses the "fire" switch, the software can check to see if the time delay has elapsed. Accordingly, if the time delay has not elapsed, the "fire" transistor/relay is not closed even if a peak lung inflation is detected. Upon the user pressing the "fire" button, on the handle, the button representing "fire" on the PC display, for example, changes color, acknowledging that the request to fire the x-ray has been received and is being processed. If the time delay has elapsed, meaning that the capacitors are charged, the transistor representing the "fire" button can be closed at the next peak lung inflation. The ability to press the "rotor-up" and "fire" buttons and have the subject device automatically fire after the capacitors are charged and at peak lung inflation can be referred to as "fire and forget." In a preferred embodiment, the user only need push one button, for example a "fire" button to initiate both the "rotor-up" function and, after an automatic time delay, the "fire" function. A buzzer can sound to indicate that the x-ray beam has been fired and the color of the "fire" button can change to yet another color to indicate the x-ray beam has been fired. In a specific embodiment FIG. 6 illustrates one example of a screen design for a PC, according to the subject invention.

In another specific embodiment, the subject invention can utilize a standard x-ray machine firing handle such that a user who has prior experience with the standard firing handle can benefit from this prior experience with respect to the subject device. In addition, the use of such a standard firing handle can be less expensive to implement than a graphical interface. In a specific embodiment utilizing a firing handle, the firing handle can have a collimator button, a rotor-up button, and a fire button. A predetermined delay, for example 3 seconds, can be implemented such that the firing handle will not fire the x-ray beam until after the predetermined delay has elapsed after pushing the rotor-up button. Accordingly, after the predetermined delay has elapsed the fire button will effect the firing of the x-ray beam upon, for example, peak lung inflation. The rotor-up and fire function can be combined into a single button such that once this multi-function button is pushed, the firing handle will cause the x-ray machine to charge up its capacitors for firing, implement the predetermined delay, and effect the firing of the x-ray beam upon the next peak lung inflation of the patient following the predetermined delay.

Additional features can be added to the firing handle, for example to provide feedback to a user. Multiple LED's can be used to provide visual feedback and/or a buzzer can be used to provide audio feedback. In a specific embodiment, a red LED lights when the collimator button is pushed, a yellow LED lights when the rotor-up button is pushed, and a green LED lights after the x-ray beam is fired. Further embodiments can utilize, for example, a two color LED which lights a first color to indicate the user has pressed the fire button and lights a second color to indicate the x-ray beam has fired. In addition, a buzzer can sound when the x-ray beam is fired to indicate it is safe for the user to enter the patient's room. An additional safety feature can be added to prevent the x-ray beam from firing again for at least a predetermined delay, for example one hour. This is to prevent unintentionally overdosing the patient with x-ray radiation.

In a specific embodiment which utilizes a flowmeter, the flowrate can be integrated over time to yield a volume inspired by the patient. This allows an adjustment to the firing algorithm where the subject device will not fire the x-ray machine until this volume inspired by the patient reaches a specific minimum value. This threshold volume can be set, for example, based on a patient's size, medical history, age, ventilation circumstance, and/or a variety of other factors. This threshold volume can help prevent firing the x-ray machine and getting a poor quality radiograph, for example, when a patient hiccups or takes a small breath which may only be a fraction of the normal size breath. A threshold inspired volume can also be indirectly inferred from the airway pressure during positive pressure ventilation, for example by setting a threshold positive pressure above baseline which corresponds to a threshold volume inspired.

In a specific embodiment, the subject device can incorporate an abort feature, for example a button on the x-ray firing handle. This abort button can enable a user to abort the process leading to the firing of the x-ray machine, for example if the patient moves during the procedure. This abort feature can also be incorporated into an embodiment of the subject device which utilizes a graphical user interface, for example displayed on a monitor of a PC. This abort feature can prevent the taking of a radiograph which a user believes will be of poor quality and can therefore save resources, time, and reduce a patient's exposure to x-rays. In a preferred embodiment, this abort feature can be implemented by requiring the user to keep the fire button continuously depressed during the period between pressing the rotor-up button and the x-ray beam firing, in order to take a radiograph. If, however, the user releases the fire button before the firing of the x-ray beam, the x-ray beam exposure will be aborted. This embodiment of the abort feature does not require an additional button on the firing handle, and can be easily understood by users.

Following are examples which illustrate procedures for practicing the subject invention. These examples should not be construed as limiting.

EXAMPLE 1

Figure 7:
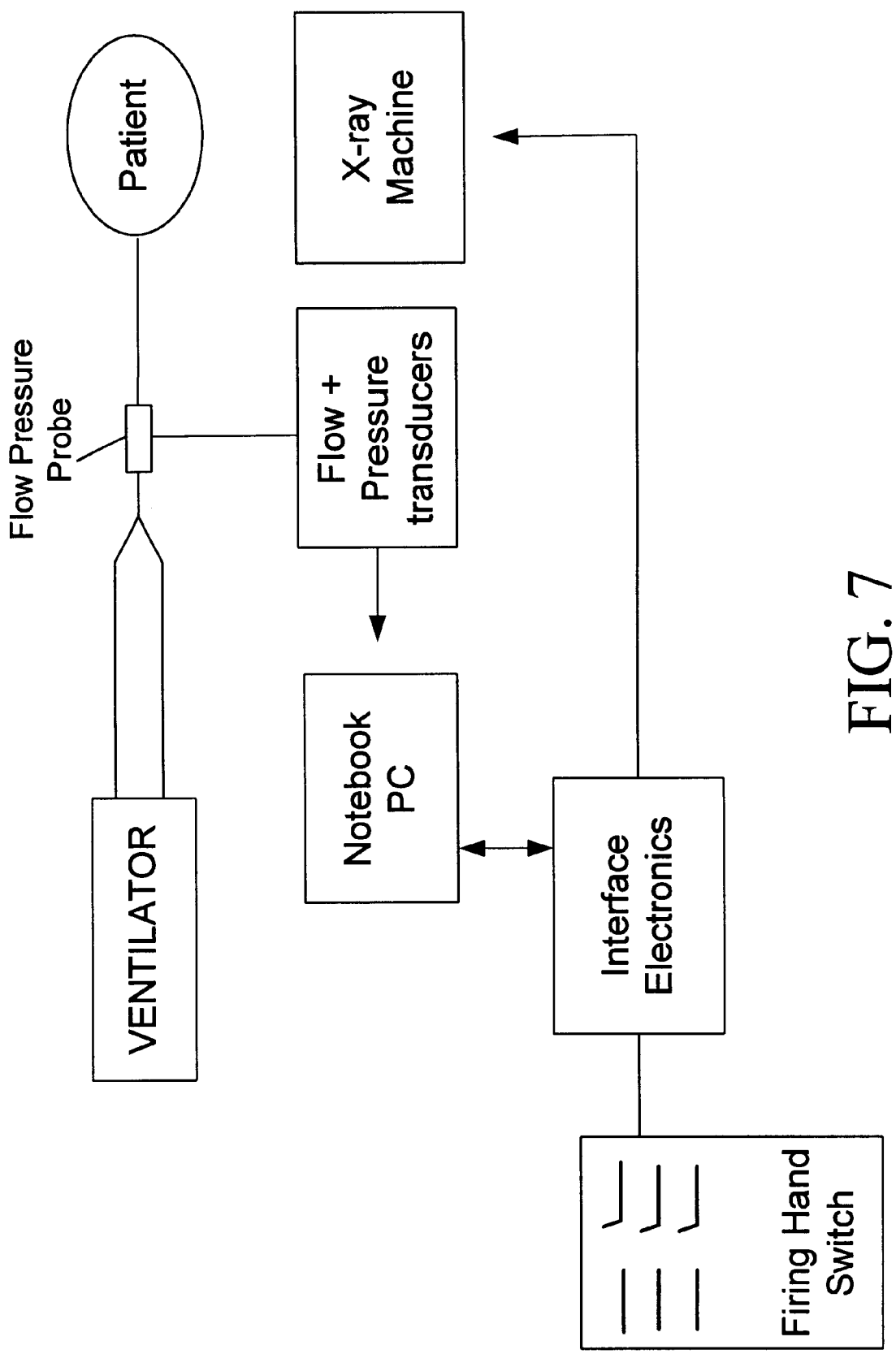
FIG. 7 is a block diagram of an embodiment of the subject invention which utilizes flow and pressure measurements to monitor lung inflation.
Figure 17:
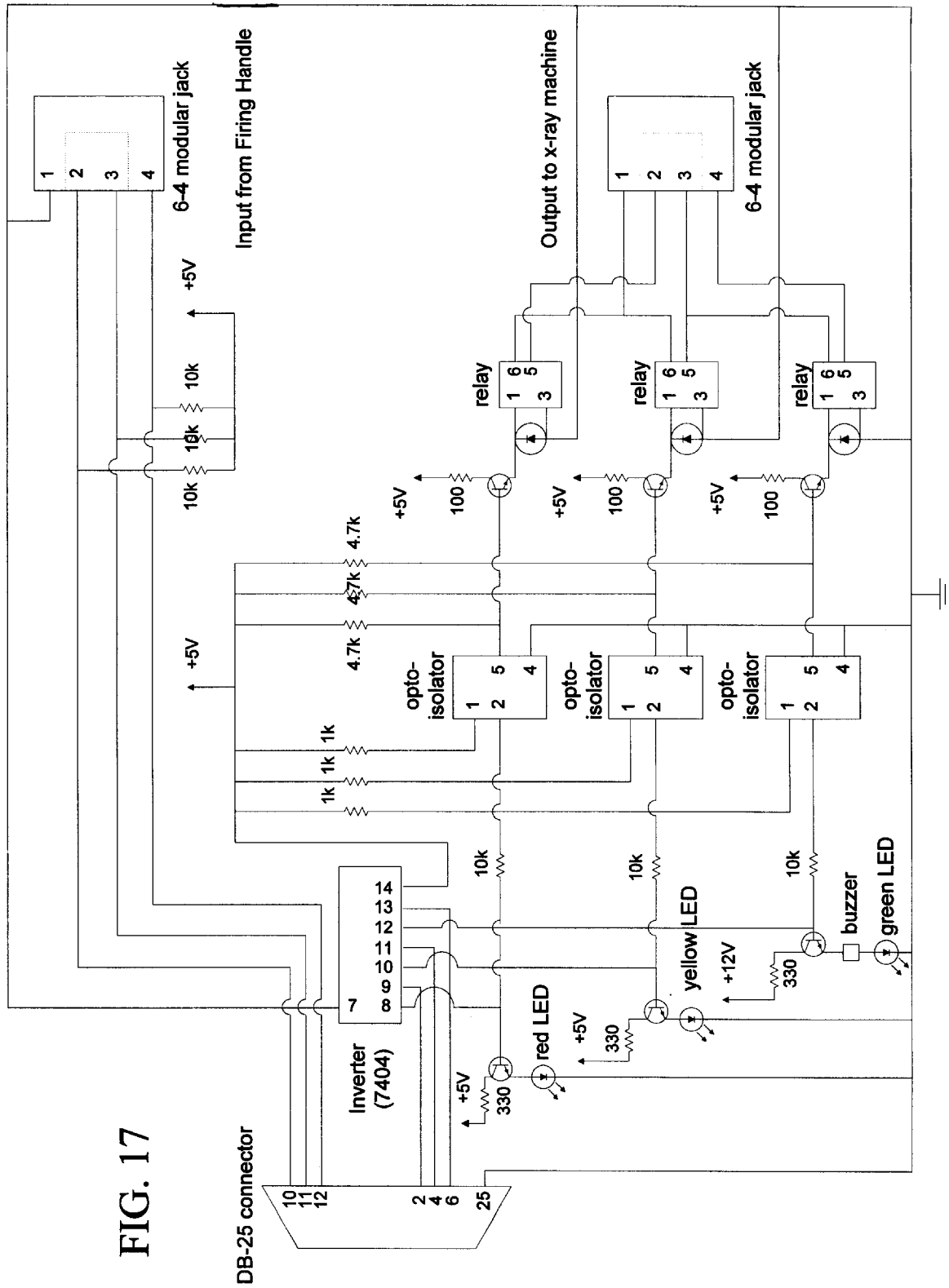
FIG. 17 is a circuit schematic for the electronic interface of a specific embodiment of the subject invention.

This example describes a preferred embodiment of the subject invention which automatically synchronizes x-ray beam exposure to a patient's peak lung inflation (PLI). FIG. 17 shows a circuit schematic for the interface electronics of the device discussed in this example. Referring to FIG. 7, this device can utilize a flowmeter, for example a Novametrix Flo Trak positioned at the airway, and can automatically fire an x-ray machine at PLI. This device can be interposed between a firing handle and a radiograph machine, and is transparent to the user except for the flowmeter at the patient's airway.

The use of a flow/pressure sensor probe allows the subject device to function with essentially any ventilator, for example electronic or pneumatic. A probe associated with the flow and pressure sensors is positioned at the airway and sends signals corresponding to the flow of gas to and from the patient as well as the airway pressure. In order to reduce noise in the flow and pressure signals, one or both signals can be low-pass filtered, for example using a software algorithm. Using pressure as an example, the filtering algorithm can take the current pressure reading, add the two previous pressure readings, and divide the total by 3 to obtain a filtered value. Flow measurements can be filtered in a similar way, for example by taking the average of the three most recent samples. The pressure measurement can be made relative to a patient's baseline pressure, where the baseline pressure is the pressure at the patient's airway when a transition from a negative to a positive flow occurs. The baseline pressure can be checked and recorded on each breath. The baseline pressure can also be referred to as positive end expiratory pressure (PEEP). Some patient's lungs should not be allowed to drop below the patient's baseline pressure. This is due to the tendency of these patients' lungs to collapse when their airway pressure drops below baseline.

The device can use the flow and pressure values, preferably filtered, from the flowmeter to determine that PLI has occurred and fire the machine. Qualitatively, the software, for example written in C, can look for an instantaneous change in gas flow direction from "towards the patient" to "away from the patient" (a falling zero flow crossing) and/or a peak pressure value, to positively identify PLI, for example during positive pressure ventilation (PPV). Each algorithm, zero-flow crossing and peak pressure, can individually detect PLI. In a preferred embodiment, both a zero-flow crossing and peak pressure can be required before firing the x-ray machine, thus improving reliability.

In order to synchronize the triggering of an x-ray machine with PLI, the subject device determines the point at which peak, or near peak, inflation occurs and triggers an x-ray machine to fire when peak, or near peak, inflation occurs. Preferably, the subject x-ray machine triggering device performs these tasks in sequence.

In addition to triggering an x-ray machine at peak inflation of the lungs, the device can also trigger a x-ray machine at other points of a patient's breathing cycle, for example at full deflation of the lungs.

Figure 10:
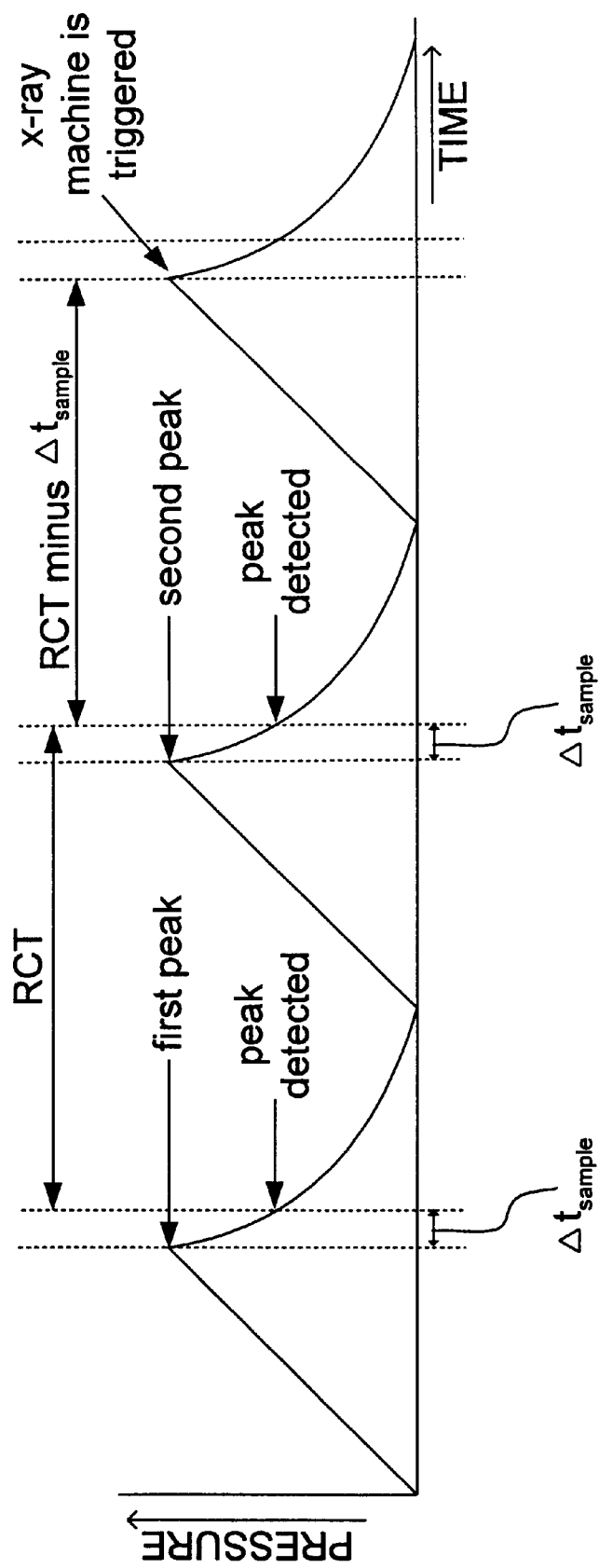
FIG. 10 illustrates a patient's airway pressure versus time for controlled mechanical ventilation (CMV) and the corresponding respiratory cycle time (RCT).

Traditionally, ventilators have a sigh switch. It is also possible to trigger an x-ray machine when a "sigh breath" is delivered from a ventilator. To reduce the chances of an x-ray image being taken with insufficient inflation of the patient's lungs, the subject device can be set to only fire the x-ray beam upon reaching a minimum lung volume, VT min, such that a quality image can be obtained. For example, this VT min can be a volume larger than normal tidal volume but smaller than the volume due to a sigh breath. Requiring a minimum lung volume before allowing an x-ray image to be taken can prevent x-ray images from being triggered by, for example, short breaths, hiccups, or other events which may satisfy the other peak lung detection criteria, for example certain zero flow crossings, when, in fact, PLI has not occurred. If a patient is on Controlled Mechanical Ventilation (CMV), the x-ray machine triggering device can predict when the next full inflation of a patient's lungs will occur, based on the respiratory cycle time (the time between two peak inflations). Referring to FIG. 10, the respiratory cycle time (RCT) for a patient on CMV is shown. A specific embodiment of the subject invention can use a predictive algorithm to determine when to fire a radiograph based on a patient's respiratory cycle time. The algorithm can determine the cycle time by measuring the amount of time that elapses between two peaks in lung pressure and then predicting when the next peak will occur by using the last peak as a reference starting point and adding the respiratory cycle time. Other points in the breathing cycle can be determined in an analogous fashion. In a specific embodiment utilizing a predictive algorithm based on RCT, peak inflation can be detected by monitoring the pressure in the patient's airway and looking for a transition from a rising pressure trend to a falling pressure trend. This falling pressure trend can be determined by requiring a certain number, for example five, consecutive falling pressure readings. However, in order to have five consecutive falling pressure readings, five sample periods must pass such that the patient is five sample time periods, $\Delta t_{sample}$, past peak lung inflation. Accordingly, once the patient's RCT is determined by calculating the time difference between two consecutive peak lung inflations (PLI), each PLI detected five sample time periods after actual PLI, this RCT minus $\Delta t_{sample}$ can be added to the time of the last detected PLI to predict the time of the next actual PLI such that, for example, an x-ray image can be taken.

In a specific embodiment, a handheld firing handle can be used to trigger, for example, a General Electric (GE AMX4) portable x-ray machine. A 10 ft standard telephone cable (handset to phone unit) can connect the firing handle to the interface electronics. The firing handle can incorporate three buttons: the collimator, the rotor up button, and the firing button. The collimator button can be used for aiming the x-ray machine. When the collimator button is pressed, a cross-hair of light can be directed from the x-ray machine to the patient's chest, thereby indicating where the radiograph will be taken. The rotor up button and the firing button can be designed to be used together in order to take a radiograph. The rotor up button can initiate the charging of one or more capacitors in the x-ray machine. When the capacitor(s) are charged, the fire button can be pressed to take a radiograph. Accordingly, the x-ray machine will not be triggered unless the rotor up button has been pressed. In a specific embodiment, the rotor up button can be positioned directly on top of the firing button, such that it is not possible to press the firing button without first pressing the rotor up button.

Figure 8:
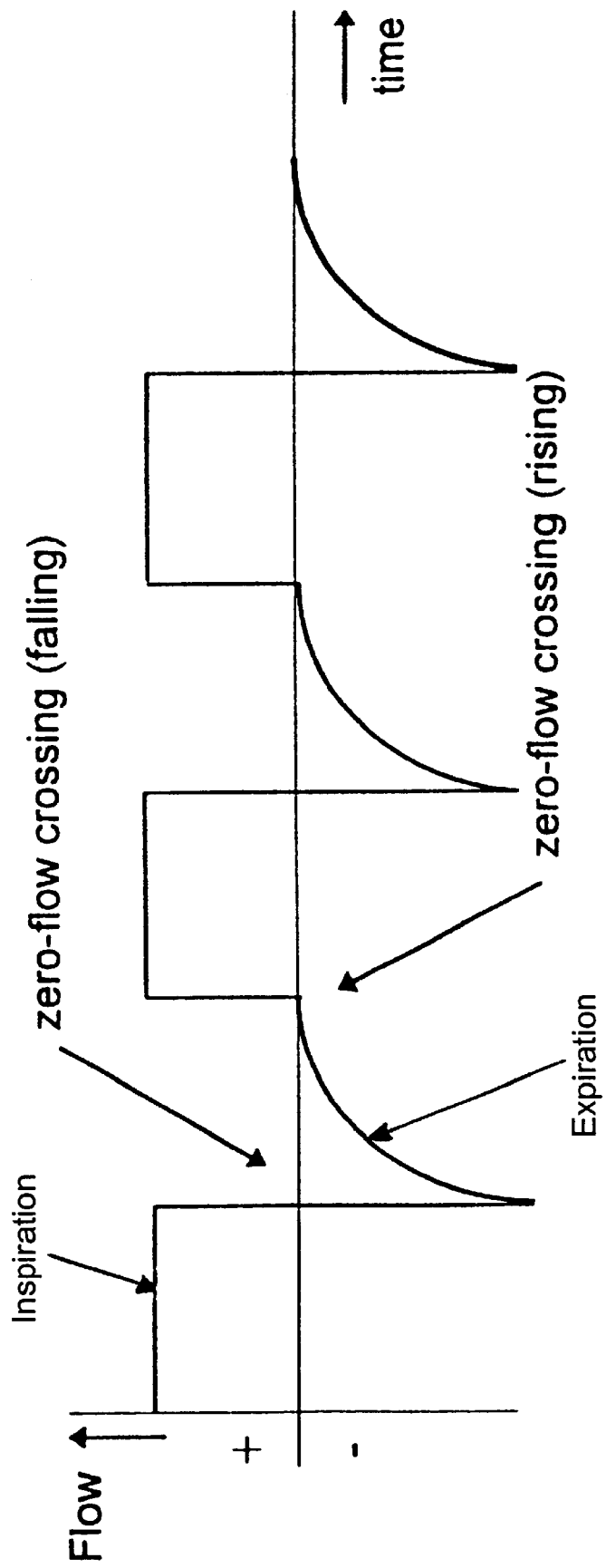
FIG. 8 shows a graph of flow versus time during positive pressure ventilation for a constant flow inspiratory waveform where flow toward patient is denoted with a plus sign and flow away from patient is denoted with a minus sign.

In a preferred embodiment, the subject device utilizes a flow/pressure sensor probe positioned between the breathing circuit and the airway device to infer peak lung inflation. By measuring flow with the flowmeter, one can infer peak lung inflation, for example, by determining when flow changes direction from a positive flow (towards patient, inspiration) to a negative flow (away from patient, expiration). This change in direction of flow is often referred to as a falling zero-flow crossing. The x-ray machine synchronization device can monitor falling zero-flow crossings, which change from positive to negative flows. Referring to FIG. 8, when such a falling zero-flow crossing occurs during positive pressure ventilation, the lungs of a patient are almost fully inflated but beginning to deflate. At this point in time, the x-ray machine synchronization device can instruct an x-ray machine to take a radiograph.

The flow/pressure sensor probe, for example the Novametrix FloTrak probe, can also measure pressure. Accordingly, the x-ray machine triggering device can use pressure as a means to deduce peak lung inflation. Referring to FIG. 9A, during positive pressure inspiration, a patient's lung pressure rises, and during expiration the lung pressure falls. By determining when peak pressure occurs, the point in time at which a patient's lungs are fully inflated can be determined. Referring to FIG. 9B, during spontaneous inspiration the pressure decreases.

In a specific embodiment, the subject x-ray machine triggering device can use both flow and pressure, simultaneously, to determine whether a patient is spontaneously breathing or under positive pressure ventilation. Subsequently, for either situation, the subject device can detect peak lung inflation. For example, a peak inflation detection algorithm for use with spontaneously breathing patients can be implemented which determines peak lung inflation has occurred upon simultaneous detection of a falling zero flow crossing and a rising pressure trend. However, it is possible to have a falling zero flow crossing and a rising pressure trend without having peak lung inflation. Accordingly, a third criteria which must also be met, for example a minimum volume of inspired gases, can be included in the peak lung inflation algorithm. In addition, a peak inflation detection algorithm for use with positive pressure ventilation can be implemented which determines peak lung inflation has occurred upon simultaneous detection of a falling zero flow crossing and a falling pressure trend. However, it is possible to have a falling zero flow crossing and a falling pressure without having peak lung inflation, for example with a small patient breath or with artifacts. Accordingly, a third criteria which must also be met, for example a minimum lung pressure, can be included in the peak inflation algorithm. This criteria can require a minimum lung pressure of, for example, 2.0 cm $H_2O$ above a patient's baseline pressure. Utilizing both airway pressure and the flow of gases into or out of the patient's airway, the subject x-ray machine triggering device can create a more robust peak inflation detection algorithm. Accordingly, when peak lung inflation is detected, the x-ray machine synchronization device triggers the x-ray machine.

Figure 11:
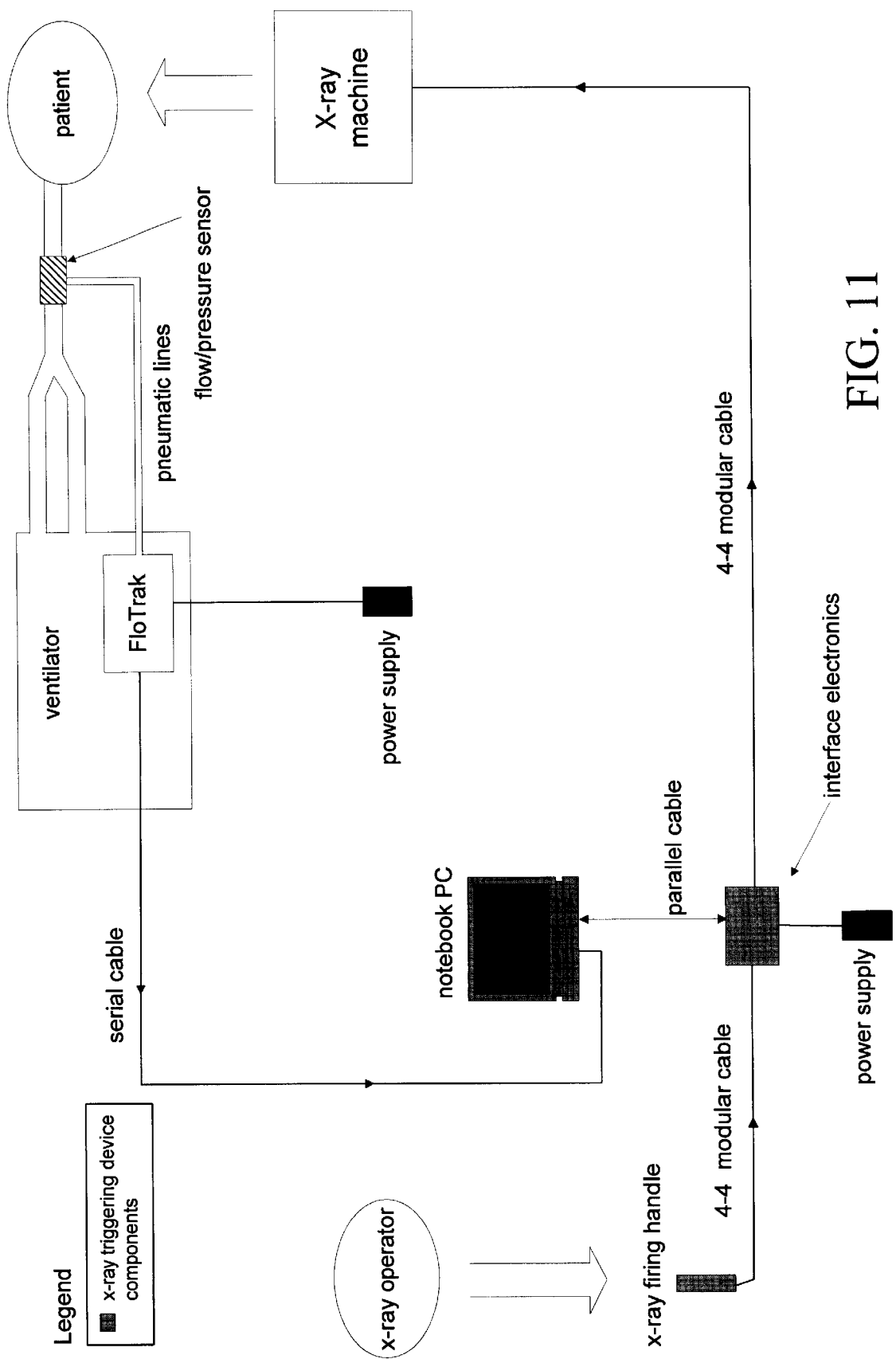
FIG. 11 illustrates how a specific embodiment of an x-ray machine triggering system interconnects with the patient, the x-ray machine operator, the ventilator, and the x-ray machine.

Referring to FIG. 11, the interface electronics of the subject device interface with a PC, an x-ray machine, and an optional x-ray firing handle. Alternatively, the PC can be replaced by a dedicated microcontroller or IC's. With respect to the device of this example, the interface electronics interact with these various components through three communication ports, including a DB-25 male connector port and two female 6-4 (6 position-4 contact) modular telephone jacks (RJ-11 jacks). The DB-25 connector allows the interface electronics to communicate with the PC via a parallel port connection. In particular, a first 6-4 RJ-11 jack is used to receive input from a handheld firing handle and a second 6-4 RJ-11 jack is used to send commands to the x-ray machine.

Figure 13:
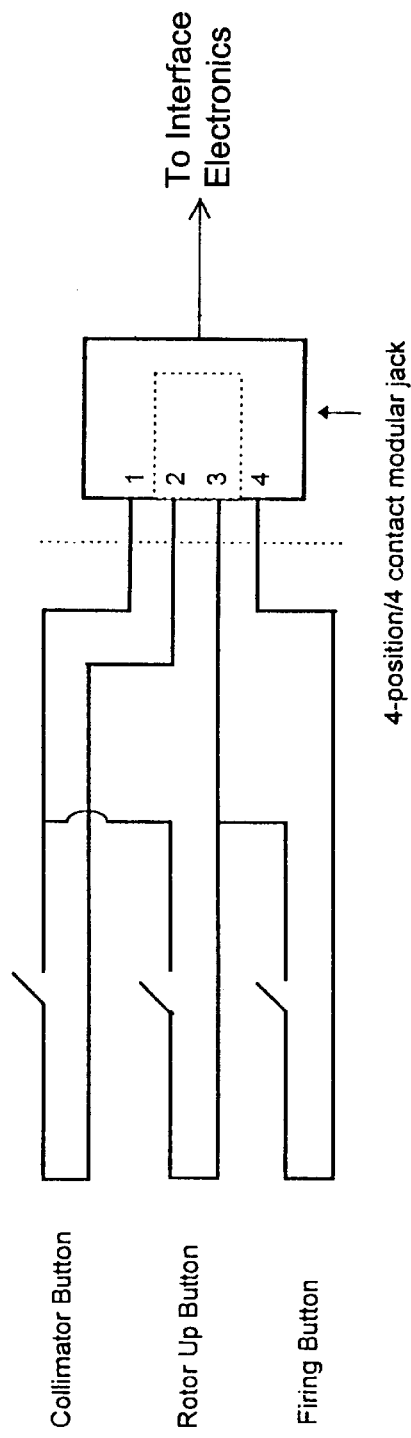
FIG. 13 illustrates the relationship between the firing handle buttons and the contacts of the modular jack connection with the interface electronics.
Figure 14:
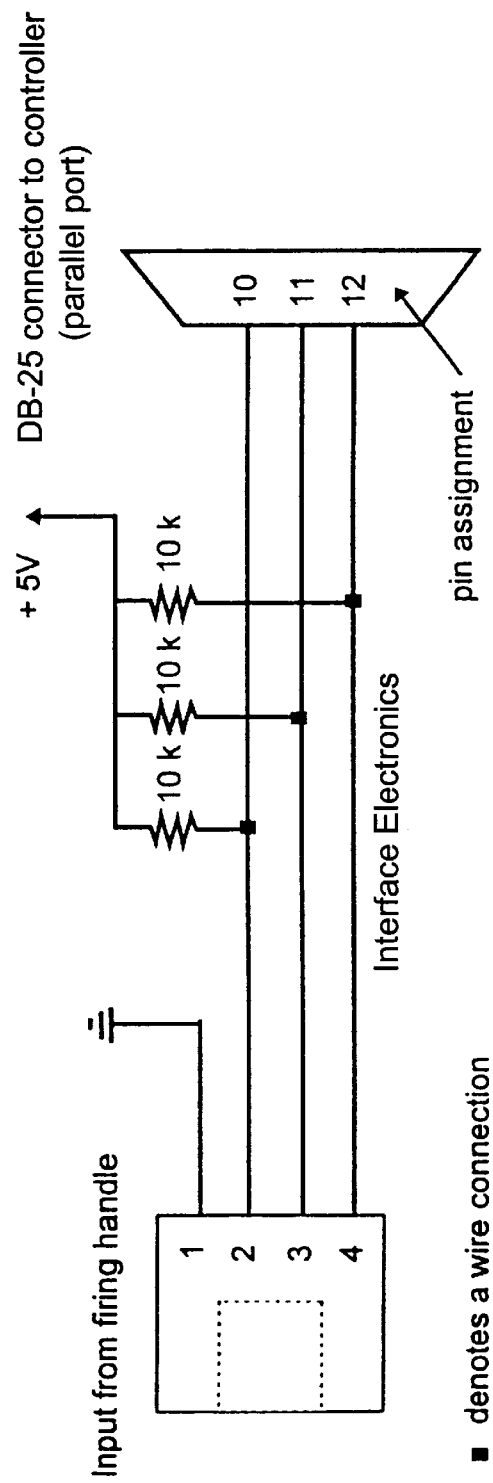
FIG. 14 shows a circuit which is a part of the interface electronics for receiving inputs from the firing handle via a modular jack, in accordance with a specific embodiment of the subject invention.

The x-ray firing handle connects to a 6-4 jack on the enclosing box for the interface electronics, for example via a 10 ft modular telephone cable. Each button on the handheld firing handle produces a short circuit between specific contacts on the 6-4 modular jack when pressed. For example, when the collimator button is pressed, the first two contacts on the 6-4 jack are shorted. Referring to FIG. 13, which contacts are closed when each of the buttons on the firing handle are pressed is shown. When a button is pressed on the firing handle, an exclusive set of contacts on the 6-4 jack is shorted. This causes an input circuit to be closed (refer to FIG. 14 for the input circuit), thereby delivering a low signal to a corresponding pin on the PC parallel port. A high signal (+2.4V to +5.0V) is sent to the same pin on the PC parallel port if the button is not being pressed. The collimator button, the rotor up button, and the firing button on the firing handle correspond to pins 10, 11, and 12 of the PC parallel port, respectively.

Figure 15:
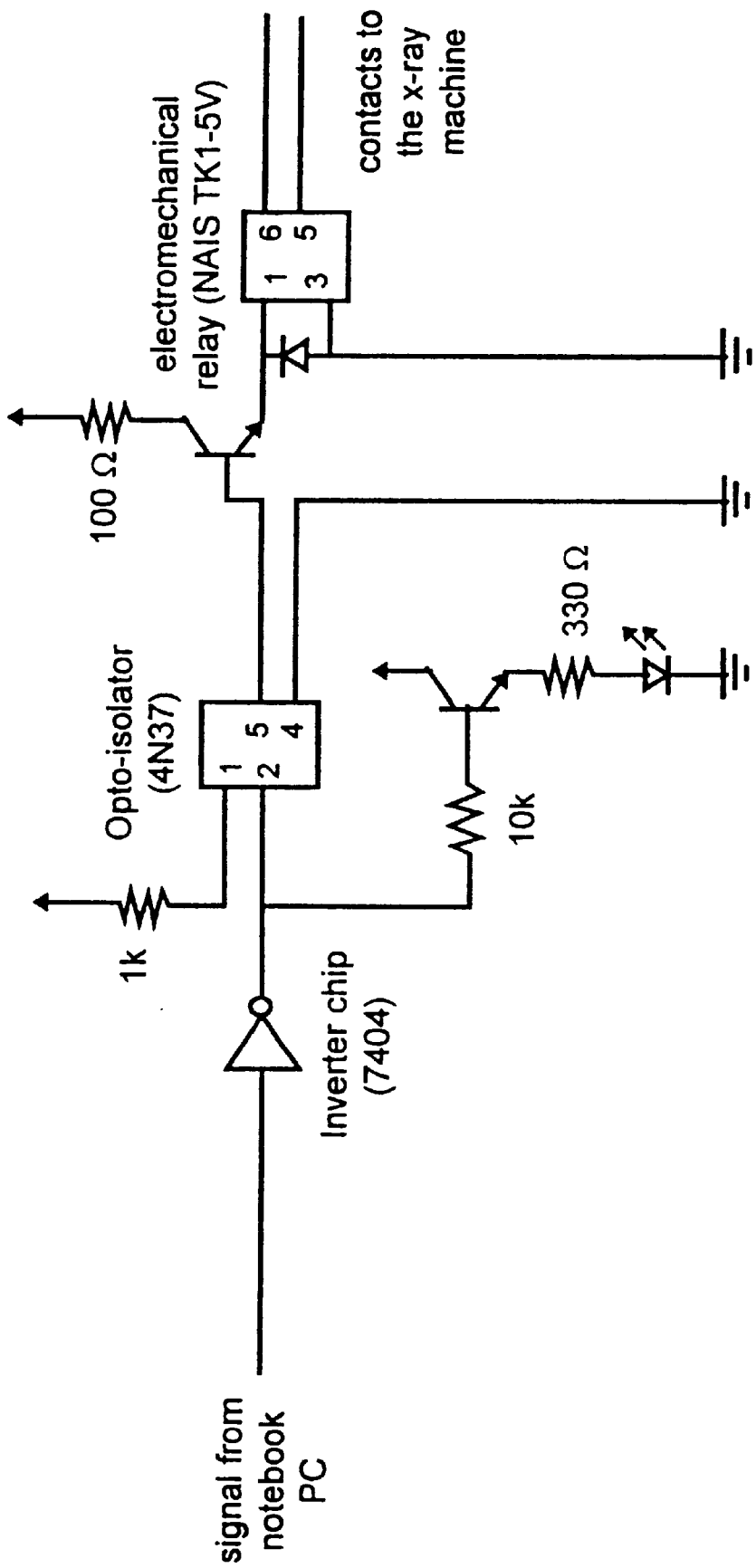
FIG. 15 shows a specific circuit of the interface electronics for transforming a signal sent from the PC to the x-ray machine, in accordance with a specific embodiment of the subject application.

The software can activate certain functions on the x-ray machine by sending low signals (0V to +0.8V) from pins 2, 4, or 6 of the PC parallel port to the interface electronics. The signals sent from pins 2, 4, and 6 of the PC parallel port can undergo a series of transformations before reaching the x-ray machine. FIG. 15 illustrates the output circuit between the PC and the x-ray machine, where the transformation of a low signal sent from. a pin on the PC parallel port takes place. Referring to FIG. 15, the low signal from the PC is inverted using a 7404 inverter chip. Alternatively, this signal ban be inverted in software. Signal inversion is performed in order to protect against the occurrence of an indeterminate state from the PC, for example if the parallel cable is accidentally detached from the PC. During an indeterminate state, a high signal is sent to the inverter chip. Thus, the purpose of the inverter chip is to prevent a high signal from being sent to, and triggering, the x-ray machine when the circuit is in an indeterminate state.

The high signal outputted from the inverter chip is inputted into an opto-isolator chip. This provides electrical isolation between the synchronization system, for example a notebook computer, and the x-ray machine. The high signal outputted from the inverter chip also actuates a NPN transistor which closes a circuit containing a 330 ohm resistor and a LED. The high signal, outputted from the opto-isolator chip, is sent to a NPN transistor which closes a circuit containing a 100 ohm resistor and a single-pole double-throw (SPDT) electromechanical relay. A clamping diode (K0462) is attached between the ground pin (pin 3) and the input pin (pin 1) of the electromechanical relay. This is done to protect circuitry from the high back-EMF which may be caused by the electromechanical relay (an inductive component).

Figure 16:
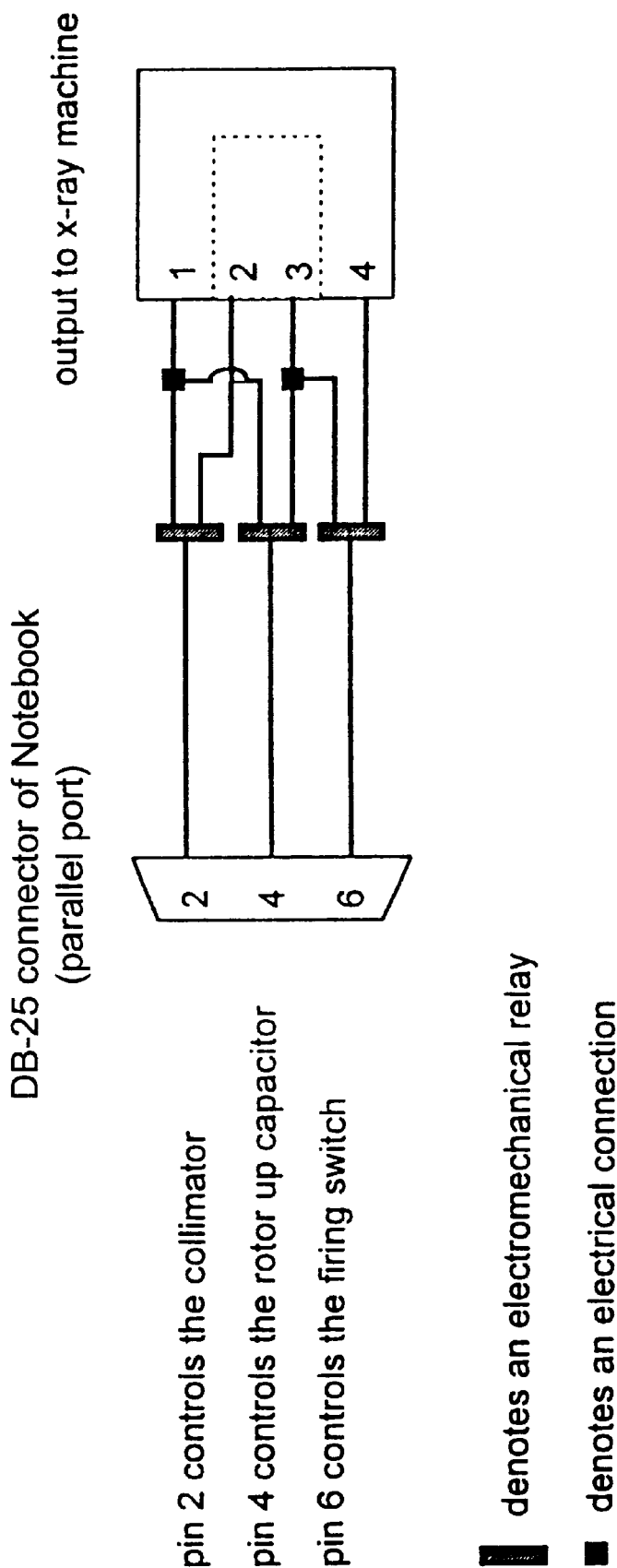
FIG. 16 illustrates the pin to contact-closing relationship between the PC and the x-ray machine, in accordance with a specific embodiment of the subject invention.

The electromechanical relay closes the appropriate contacts on the 6-4 modular jack connected to the x-ray machine. This activates the appropriate function on the x-ray machine. FIG. 16 shows which contacts are closed when a signal is sent from the PC parallel port (pins 2, 4, or 6).

Figure 12:
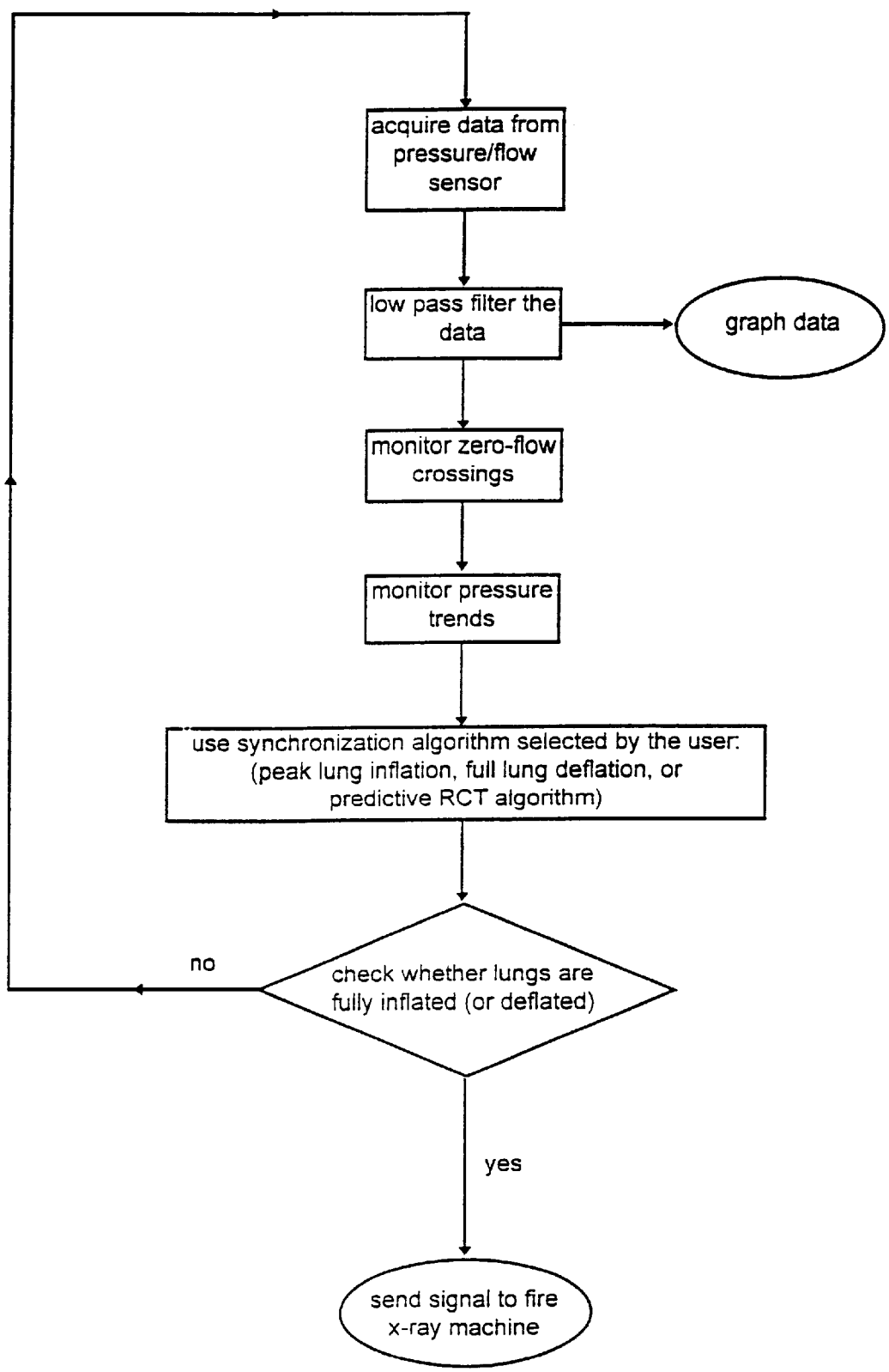
FIG. 12 is a pseudo-code flowchart for a specific embodiment of the subject invention.

With respect to this specific example, a discussion of the pseudo-code for peak lung inflation detection, full lung deflation detection, and predictive peak lung detection algorithms is presented below. FIG. 12 shows a flow chart for the device's pseudo-code.

The pseudo-code steps for peak lung inflation detection are outlined below, where the goal is to take a radiograph at peak lung inflation after detecting a falling zero-flow crossing AND peak pressure.

1) Declare and initialize variables.

2) Begin the loop

3) Obtain the current flow and pressure readings from the Novametrix FloTrak sensor and store these values in variables. Call the current flow reading "flowT" (representing flow at time t or flow(t)). Call the current pressure reading "pressureT" (representing pressure at time t or pressure(t)).

4) Filter the flow signal through a low-pass filter by taking the current flow reading, adding it to the previous two flow readings, and dividing the total by three (3). Store this filtered value in a variable called "flow" (representing the filtered flow at time t). Call the two previous flow readings "flowT_1" (representing flow at time t minus 1 or flow (t−1)) and "flowT 2" (representing flow at time t minus 2 or flow(t−2)).

If the two previous flow readings (flowT_1 and flowT_2) have not been determined yet (i.e. the detection algorithm has just started) copy the current flow reading (flowT) into the variable which stores the filtered flow value (flow).

Filter the pressure signal through a low-pass filter by taking the current pressure reading, adding it to the previous two pressure readings, and dividing the total by three (3). Store this filtered value in a variable called "pressure" (representing the filtered pressure at time t). Call the two previous pressure readings "pressureT_1" (representing pressure at time t minus one or pressure(t−1)) and "pressureT_2" (representing pressure at time t minus two or pressure(t−2)).

If the two previous pressure readings (pressureT_1 and pressureT_2) have not been determined yet (i.e. the detection algorithm has just started) copy the current pressure reading (pressureT) into the variable which stores the filtered pressure value (pressure).

5) After filtered flow and pressure signals have been calculated, update the variables storing the previous pressure and previous flow values. For example:

flowT_2=flowT_1 flowT_1=flowT pressureT_2=pressureT_1 pressureT_1=pressureT

6) Check whether a zero-flow crossing has occurred.
- if the previous filtered flow value (previousFlow) is greater than +1.0 L/min AND the current filtered flow (flow) is less than −1.0 L/min, then set a flag indicating that a zero-flow crossing (falling) has occurred. The initial value of the previousFlow variable at start up is zero.
- else, if the previous flow value (previousFlow) is less than −1.0 L/min AND the current flow (flow) is greater than +1.0 L/min, then set a flag indicating that a zero-flow crossing (rising) has occurred.

When a negative to positive change in flow occurs, the baseline pressure of the patient can be determined. Copy the current filtered pressure value (pressure) into a variable called "baselinePressure." Baseline pressure is checked and recorded on every breath.

7) Update the value of the previous flow variable (previousFlow). For example, previousFlow=flow 8) Check whether pressure is rising or falling.
- if the pressure falls for n, for example five (5), consecutive readings then set a flag indicating that there is a falling pressure trend. In order to ensure that a falling trend is not falsely detected, pressure must fall for five consecutive readings. Although it was determined, through testing, that only three consecutive readings are necessary to reliably detect a falling pressure trend, five consecutive readings are taken as a safety measure to ensure that the algorithm does not detect a false falling pressure trend.
- else, if the pressure rises for five (5) consecutive readings then set a flag indicating that there is a rising pressure trend.
- otherwise, reset the flags which indicate whether there is a rising or falling pressure trend.

9) Determine whether the patient's lungs are fully inflated.
- check the status of the flag which indicates whether there is a falling pressure trend. Also, check the status of the flag which indicates whether a zero-flow crossing (falling) has occurred.
- if a zero-flow crossing (falling) has occurred AND a falling pressure trend has occurred AND the current pressure is 2.0 cmH$_2$O above baseline pressure, then set a flag indicating that a radiograph should be taken. Break out of the loop.

10) End the loop

The pseudo-code steps for full lung deflation detection are outlined below, where the goal is to take a radiograph on full lung deflation after detecting a rising zero-flow crossing AND a rising trend in pressure. Steps 1 through 8 of the peak inflation algorithm are also used by the full lung deflation detection algorithm. The code is shared by both algorithms.

9) Determine whether the patient's lungs are fully deflated.
- check the status of the flag which indicates whether there is a rising pressure trend. Also, check the status of the flag which indicates whether a zero-flow crossing (rising) has occurred.
- if a zero-flow crossing (rising) occurs AND there is a rising trend in pressure, then set a flag indicating that a radiograph should be taken. Break out of the loop.

10) End the loop

The pseudo-code steps for predictive peak lung detection are outlined below, where the goal is to predict when peak lung inflation will occur and subsequently take a radiograph using an algorithm based on respiratory cycle time.

Steps 1 through 8 of the peak lung inflation and full lung deflation algorithms are also used by the predictive peak lung detection algorithm. The code is shared by all algorithms.

9) Determine whether the patient's lungs are fully inflated.
- check the status of the flag which indicates whether there is a falling pressure trend. Also, check the status of the flag which indicates whether a zero-flow crossing (falling) has occurred.
- if a zero-flow crossing (falling) has occurred AND a falling pressure trend has occurred AND the current pressure is 2.0 cmH$_2$O above baseline pressure, then increment the counter variable peakPressureCounter. This variable is initially set to zero (0) and is incremented each time full lung inflation is detected.

10) When full lung inflation is first detected (i.e. peakPressureCounter==1):
- save the number of processor clock ticks since the program started into the variable startCycle. For example: startCycle=clock( )
- clock( ) is a C function that returns the processor time elapsed (in clock ticks) since the beginning of the program invocation.
- change the color of the flow and pressure traces on the graphical user interface from green to red to indicate that the RCT is being measured. Also, display the message "Estimating Cycle Time" to indicate that the RCT is being measured.

11) When the second full lung inflation is detected (i.e. peakPressureCounter==2):
- save the number of processor clock ticks since the program started into the variable stopCycle. For example: stopCycle=clock( )
- compute the respiratory cycle time. Save this value in a variable called cycleTime. The variable cycleTime stores the number of processor clock ticks between the first and second full lung inflation. For example:

cycleTime=stopCycle−startCycle

- set the predicted time that the next full lung inflation should occur and save this value in the variable predictedTargetTime. The value of the predictedTargetTime variable is calculated by adding cycleTime to stopCycle. In addition, adjustments can be made to compensate for sampling times. For example:

predictedTargetTime=stopCycle (time of second full lung inflation)+cycleTime (time between first and second full lung inflations)−sampling delay (time to collect n consecutive falling pressure values)

change the color of the flow and pressure traces from red to white to indicate that the algorithm will trigger the x-ray machine on the next full lung inflation. Also display the message "Firing on the next peak."

12) When the current time (in processor ticks) equals the value of predictedTargetTime (i.e. clock( )(== predictedTargetTime), set a flag indicating that a radiograph should be taken. Break out of the loop.

13) End the loop

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A device for improving the efficacy of the taking of a chest image, comprising:
    a means for receiving a signal from a ventilator, wherein said signal carries information relating to the ventilation of the patient with a sigh breath;
    a means for effecting the taking of a chest image with respect to the patient, wherein said device improves the efficacy of the taking of a chest image by coordinating the taking of a chest image with the delivery of a sigh breath to the patient; and
    a means for causing the ventilator to ventilate the patient with a sigh breath, wherein said means for effecting the taking of a chest image effects the taking of a chest image when the signal indicates the patient is ventilated with a sigh breath such that a chest image of the patient is taken at peak lung inflation.

2. A device for improving the efficacy of the taking of an image, comprising:
    a means for receiving a signal, wherein said signal carries information relating to a patient's breathing cycle,
    a means for effecting the taking of an image with respect to the patient,
    wherein said device improves the efficacy of the taking of an image by coordinating the taking of an image to the patient's breathing cycle wherein said device can determine at least one point in the breathing cycle of the patient based on the information carried by said signal, wherein said means for effecting the taking of an image with respect to said patient effects the taking of an image based on said point(s) in the breathing cycle, wherein said means for effecting the taking of an image effects the taking of an image at a desired point in the breathing cycle of the patient wherein said means for effecting the taking of an image comprises;
        a means for sending a rotor-up signal to an x-ray machine;
        a means for sending an output signal to the x-ray machine; and:
        a means for receiving caregiver input, wherein a caregiver can input a rotor-up command, wherein upon the input of the rotor-up command, said means for sending a rotor-up signal to an x-ray machine sends a rotor-up signal to the x-ray machine which initiates the charging of a capacitor of the x-ray machine in order to prepare for firing, and wherein the caregiver can input a fire command wherein upon the input of the fire command said means for sending an output signal to the x-ray machine sends an output signal to the x-ray machine when said signal indicates the desired point in the breathing cycle wherein the sending of the output signal to the x-ray machine effects the taking of an image at the desired point in the breathing cycle.

3. The device, according to claim 2, wherein said means for receiving caregiver input is a firing handle.

4. The device, according to claim 3, wherein the means for receiving caregiver input is adapted to receive input of the rotor-up and fire commands simultaneously.

5. The device, according to claim 4, wherein the means for receiving caregiver input is adapted to receive input of the rotor-up and fire commands by the pressing of a single button.

6. The device, according to claim 3, wherein said firing handle further comprises an abort input means, wherein said abort input means enables the caregiver to abort the sending of the output signal.

7. The device, according to claim 2, wherein the means for effecting a diagnostic procedure is adapted such that, after the caregiver inputs the fire command, the means for effecting a diagnostic procedure will delay sending the output signal for at least a predetermined period of time after selection of the rotor-up command.

8. The device, according to claim 7, wherein said predetermined period of time is at least three seconds.

9. The device, according to claim 7, wherein the means for receiving caregiver input is adapted such that the caregiver inputs the fire command by pressing a fire button, and wherein the means for effecting a diagnostic procedure is adapted such that the caregiver must continuously press the fire button until said means for effecting a diagnostic procedure sends the output signal or the sending of the output signal will be aborted.

10. The device, according to claim 2, wherein said means for receiving caregiver input is a graphical user interface.

11. A device for improving the efficacy of a medical treatment or diagnostic procedure, comprising:
    a means for receiving a signal from a ventilator, wherein said signal carries information relating to a patient's breathing cycle,
    a means for effecting a medical treatment or diagnostic procedure with respect to the patient, wherein said device improves the efficacy of the medical treatment or diagnostic procedure by coordinating the medical treatment or diagnostic procedure to the patient's breathing cycle, and
    a ventilator model selector switch comprising settings corresponding to specific ventilators such that said device can interpret the signal indicating the point in the breathing cycle of the patient received from a selected ventilator.

12. A device for improving the efficacy of a medical treatment or diagnostic procedure, comprising:
    a means for receiving a signal, wherein said signal carries information relating to a patient's breathing cycle,
    a means for effecting a medical treatment or diagnostic procedure with respect to the patient, wherein said device improves the efficacy of the medical treatment or diagnostic procedure by coordinating the medical treatment or diagnostic procedure to the patient's breathing cycle, and a means for determining whether the patient is spontaneously breathing or under positive pressure ventilation, wherein said means for determining whether the patient is spontaneously breathing or under positive pressure ventilation interprets the information relating to the patient's breathing cycle to make such determination.

13. The device, according to claim 12, wherein said signal carries information with respect to the flow of gases into or out of the patient's airway and the pressure at the patient's airway.

14. The device, according to claim 13, wherein said means for determining whether the patient is spontaneously breathing or under positive pressure ventilation determines that the patient is spontaneously breathing when the flow of gases is into the patient's airway and the pressure at the patient's airway is below a baseline airway pressure for the patient.

15. The device, according to claim 14, further comprising a means for detecting peak lung inflation, wherein for a patient determined to be spontaneously breathing, said means for detecting peak lung inflation determines peak lung inflation is detected when a falling zero flow crossing and a rising pressure trend occurs.

16. The device, according to claim 15, wherein said means for detecting peak lung inflation also requires the patient to have inspired a minimum volume of gases in order to determine peak lung inflation is detected.

17. The device, according to claim 13, wherein said means for determining whether the patient is spontaneously breathing or under positive pressure ventilation determines that the patient is under positive pressure ventilation when the flow of gases is into the patient's airway and the pressure at the patient's airway is above a baseline airway pressure for the patient.

18. The device, according to claim 17, further comprising a means for detecting peak lung inflation, wherein for a patient determined to be under positive pressure ventilation, said means for detecting peak lung inflation determines peak lung inflation is detected when a falling zero flow crossing and a falling pressure trend occurs.

19. The device, according to claim 18, wherein said means for detecting peak lung inflation also requires that the pressure at the patient's airway is at least a minimum amount above a baseline airway pressure for the patient in order to determine peak lung inflation is detected.

20. A method for improving the efficacy of the taking of a chest image, comprising the following steps:
receiving a signal from a ventilator, wherein said signal carries information relating to a patient's breathing cycle effecting the taking of a chest image with respect to said patient based on the information carried by said signal, wherein said method improves the taking of a chest image by coordinating the taking of a chest image to the patient's breathing cycle, and
causing the ventilator to ventilate the patient with a sigh breath,
wherein the taking of a chest image is effected when the patient is ventilated with a sigh breath such that the chest image of the patient is taken at peak lung inflation.

21. A method for improving the efficacy of the taking of an image, comprising the following steps:
receiving a signal, wherein said signal carries information relating to a patient's breathing cycle;
effecting the taking of an image with respect to said patient based on the information carried by said signal, wherein said method improves the efficacy of the taking of an image by coordinating the taking of an image to the patient's breathing cycle, wherein the step of effecting the taking of an image effects the taking of an image at a desired point in the breathing cycle of the patient, wherein said step of effecting the taking of an image effects the sending of an output signal to an x-ray machine, and receiving input from a caregiver, wherein a caregiver can input a rotor-up command which initiates the charging of a capacitor of the x-ray machine in order to prepare for firing and wherein the caregiver can input a fire command such that said output signal is sent to the x-ray machine when said signal indicates the desired point in the breathing cycle.

22. The method, according to claim 21, wherein said input is inputted via a firing handle.

23. The method, according to claim 22, wherein said firing handle is emulated by a graphical user interface.

24. The method, according to claim 21, wherein after the caregiver inputs the fire command, further comprising the step of:
delaying the sending of the output signal until at least a predetermined period of time after input of the rotor-up command has lapsed.

25. The method, according to claim 24, wherein input of the rotor-up and fire commands is simultaneous.

26. The method, according to claim 25, wherein input of the rotor-up and fire commands is accomplished by pressing a single button.

27. The method, according to claim 24, wherein said predetermined period of time is at least three seconds.

28. The method, according to claim 21, wherein said caregiver can input an abort command which aborts the sending of the output signal.

29. The method, according to claim 21, wherein the caregiver selects the fire command by pressing a fire button, and wherein the caregiver must continuously press the fire button until said output signal is sent to the x-ray machine or the sending of the output signal will be aborted.

30. A method for improving the efficacy of a medical treatment or diagnostic procedure, comprising the following steps:
receiving a signal from a ventilator, wherein said signal carries information relating to a patient's breathing cycle,
effecting a medical treatment or diagnostic procedure with respect to said patient based on the information carried by said signal,
wherein said method improves the efficacy of said medical treatment or diagnostic procedure by coordinating said medical treatment or diagnostic procedure to the patient's breathing cycle, and selecting a specific ventilator model, corresponding to the patient's ventilator, on a ventilator model selector switch comprising settings corresponding to specific ventilator models such that said signal carrying information relating to the breathing cycle of the patient received from the ventilator can be interpreted.

31. A method for improving the efficacy of a medical treatment or diagnostic procedure, comprising the following steps:
receiving a signal, wherein said signal carries information with respect to the flow of gases into or out of the patient's airway,
receiving a second signal, wherein said second signal indicates the pressure at the patient's airway,
effecting a medical treatment or diagnostic procedure with respect to said patient based on the information carried by said signal, wherein said method improves the efficacy of said medical treatment or diagnostic procedure by coordinating said medical treatment of diagnostic procedure to the patient's breathing cycle based on the flow of gases into or out of the patient's airway and on the pressure at the patient's airway, wherein the medical treatment or diagnostic procedure is effected when the signal and the second signal indicate a desired point in the patient's breathing cycle; and determining whether the patient is spontaneously breathing or under positive pressure ventilation, wherein said step of determining whether the patient is spontaneously breathing or under positive pressure ventilation utilizes the information relating to the patient's breathing activity to make such a determination.

32. The method, according to claim 31, wherein said step for determining whether the patient is spontaneously breathing or under positive pressure ventilation determines that the patient is spontaneously breathing when the flow of gases is into the patient's airway and the pressure at the patient's airway is below a baseline airway pressure for the patient.

33. The method, according to claim 32, wherein for a patient determined to be spontaneously breathing, peak lung inflation is detected when a falling zero flow crossing and a rising pressure trend simultaneously occurs.

34. The method, according to claim 33, wherein peak lung inflation detection also requires the patient to have inspired a minimum volume of gases.

35. The method, according to claim 31, wherein said step for determining whether the patient is spontaneously breathing or under positive pressure ventilation determines that the patient is under positive pressure ventilation when the flow of gases is into the patient's airway and the pressure at the patient's airway is above a baseline airway pressure for the patient.

36. The method, according to claim 35, wherein for a patient determined to be under positive pressure ventilation, peak lung inflation is detected when a falling zero flow crossing and a falling pressure trend simultaneously occur.

37. The method, according to claim 36, wherein peak lung inflation detection also requires that the pressure at the patient's airway is at least a minimum amount above a baseline airway pressure for the patient.

* * * * *

UNITED STATES PATENT AND TRADEMARK OFFICE
CERTIFICATE OF CORRECTION

PATENT NO. : 6,597,939 B1
DATED : July 22, 2003
INVENTOR(S) : Samsun Lampotang and Paul B. Langevin It is certified that error appears in the above-identified patent and that said Letters Patent is hereby corrected as shown below:

<u>Column 15,</u>
Line 3, "simultaneously,to" should read -- simultaneously, to --.

<u>Column 16,</u>
Line 8, "ban be" should be -- can be --.
Line 59, "flowT 2" should be -- *flowT_2* --.

<u>Column 19,</u>
Lines 57-58, "breathing cycle of the patient wherein said means for effecting the taking of an image comprises;" should read -- breathing cycle of the patient; --.

<u>Column 22,</u>
Line 67, "by said signal," should read -- by said signal and said second signal, --.

<u>Column 23,</u>
Line 3, "medical treatment of diagnostic" should read -- medical treatment or diagnostic --.

Signed and Sealed this

Thirtieth Day of March, 2004

JON W. DUDAS
*Acting Director of the United States Patent and Trademark Office*